US010555698B2

(12) United States Patent
Russell et al.

(10) Patent No.: US 10,555,698 B2
(45) Date of Patent: *Feb. 11, 2020

(54) SLEEP SCORING BASED ON PHYSIOLOGICAL INFORMATION

(71) Applicant: Fitbit, Inc., San Francisco, CA (US)

(72) Inventors: Allison Maya Russell, San Francisco, CA (US); Zachary Todd Beattie, Pleasant Hill, CA (US); Alexander Statan, Oakland, CA (US); Emma Jane Quinn, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,139

(22) Filed: Oct. 9, 2018

(65) Prior Publication Data
US 2019/0254589 A1    Aug. 22, 2019

Related U.S. Application Data

(63) Continuation of application No. 15/456,494, filed on Mar. 11, 2017, now Pat. No. 10,111,615.

(51) Int. Cl.
*A61B 5/00* (2006.01)
*A61B 5/02* (2006.01)
(Continued)

(52) U.S. Cl.
CPC .............. *A61B 5/4806* (2013.01); *A61B 5/02* (2013.01); *A61B 5/4815* (2013.01); *A61B 5/681* (2013.01);
(Continued)

(58) Field of Classification Search
CPC .................................. A61K 6/00; A61B 1/00
See application file for complete search history.

(56) References Cited

U.S. PATENT DOCUMENTS

| 4,836,219 A | 6/1989 | Hobson |
| 5,724,990 A | 3/1998 | Ogino |

(Continued)

FOREIGN PATENT DOCUMENTS

| CN | 105446480 | 3/2016 |
| WO | 2008194400 | 8/2008 |

(Continued)

OTHER PUBLICATIONS

Requirement for Restriction/Election issued in U.S. Appl. No. 14/859,192 dated Jan. 22, 2016.
(Continued)

*Primary Examiner* — Shirley Lu
(74) *Attorney, Agent, or Firm* — Hogan Lovells US LLP

(57) ABSTRACT

Assessing the sleep quality of a user in association with an electronic device with one or more physiological sensors includes detecting an attempt by the user to fall asleep, and collecting physiological information associated with the user. The disclosed method of assessing sleep quality may include determining respective values for one or more sleep quality metrics, including a first set of sleep quality metrics associated with sleep quality of a plurality of users, and a second set of sleep quality metrics associated with historical sleep quality of the user, based at least in part on the collected physiological information and at least one wakeful resting heart rate of the user, and determining a unified score for sleep quality of the user, based at least in part on the respective values of the one or more sleep quality metrics.

20 Claims, 11 Drawing Sheets

(51) Int. Cl.
  *A61B 5/0205* (2006.01)
  *A61B 5/04* (2006.01)
(52) U.S. Cl.
  CPC .......... *A61B 5/6824* (2013.01); *A61B 5/0004* (2013.01); *A61B 5/0205* (2013.01); *A61B 5/04001* (2013.01); *A61B 5/486* (2013.01); *A61B 5/742* (2013.01); *A61B 5/744* (2013.01); *A61B 5/7405* (2013.01); *A61B 5/7475* (2013.01); *A61B 2505/07* (2013.01)

(56) References Cited

U.S. PATENT DOCUMENTS

| | | |
|---|---|---|
| 5,902,250 A | 5/1999 | Verrier |
| 6,011,477 A | 1/2000 | Teodorescu |
| 6,104,294 A | 8/2000 | Andersson |
| 6,893,396 B2 | 5/2005 | Schulze |
| 6,964,641 B2 | 11/2005 | Cho |
| 7,246,064 B1 | 7/2007 | Thomas |
| 7,524,279 B2 | 4/2009 | Auphan |
| 7,578,793 B2 | 8/2009 | Tadros |
| 7,859,419 B2 | 12/2010 | Shen-Kuen |
| 7,967,739 B2 | 6/2011 | Auphan |
| 8,002,553 B2 | 8/2011 | Hatlestad |
| 8,273,035 B2 | 9/2012 | Russo |
| 8,348,840 B2 | 1/2013 | Heit |
| 8,398,538 B2 | 3/2013 | Dothie |
| 8,594,982 B2 | 11/2013 | Mott |
| 8,606,356 B2 | 12/2013 | Lee |
| 8,690,751 B2 | 4/2014 | Auphan |
| 8,793,522 B2 | 7/2014 | Rahman |
| 8,882,684 B2 | 11/2014 | Halperin |
| 8,942,779 B2 | 1/2015 | Halperin |
| 9,167,991 B2 | 10/2015 | Yuen |
| 9,204,806 B2 | 12/2015 | Stivoric |
| 9,326,364 B2 | 4/2016 | Maeda |
| 9,345,433 B1 | 5/2016 | Shinozuka |
| 9,360,351 B2 | 6/2016 | Van Thienen |
| 9,610,030 B2 | 4/2017 | Proud |
| 9,675,281 B2 | 6/2017 | Arnold |
| 9,808,185 B2 | 11/2017 | Arnold et al. |
| 2003/0145854 A1 | 8/2003 | Hickle |
| 2004/0087878 A1 | 5/2004 | Krausman |
| 2004/0133081 A1 | 7/2004 | Teller |
| 2004/0172290 A1 | 9/2004 | Leven |
| 2005/0033200 A1 | 2/2005 | Soehren |
| 2005/0043652 A1 | 2/2005 | Lovett |
| 2005/0113650 A1 | 5/2005 | Pacione |
| 2005/0143617 A1 | 6/2005 | Auphan |
| 2005/0209511 A1 | 9/2005 | Heruth |
| 2005/0209512 A1 | 9/2005 | Heruth |
| 2006/0020177 A1 | 1/2006 | Seo |
| 2006/0030891 A1 | 2/2006 | Saltzstein |
| 2006/0031102 A1 | 2/2006 | Teller |
| 2006/0159645 A1 | 7/2006 | Miller |
| 2006/0224051 A1 | 10/2006 | Teller |
| 2006/0281978 A1 | 12/2006 | Crucilla |
| 2007/0191742 A1 | 8/2007 | Park |
| 2007/0208233 A1 | 9/2007 | Kovacs |
| 2007/0243851 A1 | 10/2007 | Shoarinejad |
| 2008/0012701 A1 | 1/2008 | Kass |
| 2008/0146892 A1 | 6/2008 | LeBoeuf |
| 2008/0306351 A1 | 12/2008 | Izumi |
| 2009/0145225 A1 | 6/2009 | Nasiri |
| 2009/0203972 A1 | 8/2009 | Heneghan |
| 2009/0264715 A1 | 10/2009 | Auphan |
| 2009/0299645 A1 | 12/2009 | Colby |
| 2009/0307179 A1 | 12/2009 | Colby |
| 2009/0307180 A1 | 12/2009 | Colby |
| 2009/0307181 A1 | 12/2009 | Colby |
| 2010/0056907 A1 | 3/2010 | Rappaport |
| 2010/0102130 A1 | 4/2010 | Madej |
| 2010/0153269 A1 | 6/2010 | McCabe |
| 2010/0295684 A1 | 11/2010 | Hsieh |
| 2010/0309000 A1 | 12/2010 | Munthe-Kaas |
| 2011/0015495 A1 | 1/2011 | Dothie |
| 2011/0093729 A1 | 4/2011 | Mucignat |
| 2011/0098593 A1 | 4/2011 | Low |
| 2011/0190594 A1 | 8/2011 | Heit |
| 2011/0230790 A1 | 9/2011 | Kozlov |
| 2011/0252684 A1 | 10/2011 | Ufer |
| 2011/0295083 A1 | 12/2011 | Doelling |
| 2012/0142443 A1 | 6/2012 | Savarese |
| 2012/0146795 A1 | 6/2012 | Margon |
| 2012/0179061 A1* | 7/2012 | Ramanan ............ A61M 16/024 600/538 |
| 2012/0191425 A1 | 7/2012 | Mott |
| 2012/0194419 A1 | 8/2012 | Osterhout |
| 2012/0201378 A1 | 8/2012 | Nabeel |
| 2012/0229270 A1 | 9/2012 | Morley |
| 2012/0253142 A1 | 10/2012 | Meger |
| 2012/0253489 A1 | 10/2012 | Dugan |
| 2012/0296156 A1* | 11/2012 | Auphan ................ A61M 21/02 600/28 |
| 2012/0316455 A1 | 12/2012 | Rahman |
| 2012/0316471 A1 | 12/2012 | Rahman |
| 2012/0316845 A1 | 12/2012 | Grey |
| 2013/0018284 A1 | 1/2013 | Kahn |
| 2013/0060097 A1 | 3/2013 | Rubin |
| 2013/0096843 A1 | 4/2013 | Yuen |
| 2013/0127980 A1 | 5/2013 | Haddick |
| 2013/0158368 A1 | 6/2013 | Pacione |
| 2013/0289932 A1 | 10/2013 | Baechler |
| 2013/0326790 A1 | 12/2013 | Cauwels |
| 2013/0332195 A1 | 12/2013 | Galuten |
| 2013/0338446 A1 | 12/2013 | Van Vugt |
| 2014/0089243 A1 | 3/2014 | Oppenheimer |
| 2014/0125620 A1 | 5/2014 | Panther |
| 2014/0164611 A1 | 6/2014 | Molettiere |
| 2014/0236036 A1 | 8/2014 | De Haan |
| 2014/0265642 A1 | 9/2014 | Utley |
| 2014/0266939 A1 | 9/2014 | Baringer |
| 2014/0275854 A1* | 9/2014 | Venkatraman ......... A61B 5/721 600/301 |
| 2014/0316305 A1 | 10/2014 | Venkatraman |
| 2014/0316584 A1 | 10/2014 | Matsuoka |
| 2014/0335490 A1 | 11/2014 | Baarman |
| 2014/0343380 A1 | 11/2014 | Carter |
| 2014/0364770 A1 | 12/2014 | Slonneger |
| 2014/0371635 A1 | 12/2014 | Shinar |
| 2015/0057967 A1 | 2/2015 | Albinali |
| 2015/0094914 A1 | 4/2015 | Abreu |
| 2015/0164238 A1 | 6/2015 | Benson |
| 2015/0173671 A1 | 6/2015 | Paalasmaa |
| 2015/0182163 A1 | 7/2015 | Utter |
| 2015/0182164 A1 | 7/2015 | Utter, II |
| 2015/0186609 A1 | 7/2015 | Utter, II |
| 2015/0238139 A1 | 8/2015 | Raskin |
| 2015/0320588 A1 | 11/2015 | Connor |
| 2015/0355612 A1 | 12/2015 | Franceschetti |
| 2016/0007934 A1 | 1/2016 | Arnold |
| 2016/0022175 A1 | 1/2016 | Arnold |
| 2016/0022203 A1 | 1/2016 | Arnold |
| 2016/0022218 A1* | 1/2016 | Hayes .................... A61G 7/005 600/301 |
| 2016/0051184 A1 | 2/2016 | Wisbey |
| 2016/0151603 A1 | 6/2016 | Shouldice |
| 2016/0183870 A1 | 6/2016 | Proud |
| 2016/0192876 A1 | 7/2016 | Proud |
| 2016/0198129 A1 | 7/2016 | Proud |
| 2016/0220177 A1 | 8/2016 | Proud |
| 2016/0235359 A1 | 8/2016 | Cho |
| 2016/0249854 A1 | 9/2016 | Proud |
| 2016/0270718 A1 | 9/2016 | Heneghan et al. |
| 2016/0374569 A1 | 12/2016 | Breslow |
| 2017/0025028 A1 | 1/2017 | Hrushesky |
| 2017/0182103 A1 | 6/2017 | Nguyen |
| 2017/0312477 A1 | 11/2017 | Hashizaki |
| 2017/0347946 A1 | 12/2017 | Arnold |
| 2017/0347949 A1 | 12/2017 | Arnold |
| 2017/0352287 A1 | 12/2017 | Arnold |
| 2018/0064388 A1 | 3/2018 | Heneghan |

(56) References Cited

U.S. PATENT DOCUMENTS

FOREIGN PATENT DOCUMENTS

| WO | 2380493 | 10/2011 |
| WO | 101439463 | 9/2014 |
| WO | 2016/109807 | 7/2016 |
| WO | 2017/190085 | 11/2017 |
| WO | 2018/048951 | 3/2018 |
| WO | 2015/119726 | 8/2018 |

OTHER PUBLICATIONS

Non-Final Office Action issued in U.S. Appl. No. 14/859,192 dated Jun. 24, 2016.
Non-Final Office Action issued in U.S. Appl. No. 14/859,192 dated Feb. 8, 2017.
Notice of Allowance issued in U.S. Appl. No. 14/859,192 dated Aug. 17, 2017.
Requirement for Restriction/Election issued in U.S. Appl. No. 14/877,912 dated Feb. 4, 2016.
Non-Final Office Action issued in U.S. Appl. No. 14/877,912 dated Apr. 18, 2016.
Final Office Action issued in U.S. Appl. No. 14/877,912 dated Dec. 1, 2016.
Non-Final Office Action issued in U.S. Appl. No. 14/877,912 dated Jul. 24, 2017.
Non-Final Office Action issued in U.S. Appl. No. 14/877,912 dated Jan. 25, 2018.
Notice of Allowance issued in U.S. Appl. No. 14/877,912 dated May 11, 2018.
Requirement for Restriction/Election issued in U.S. Appl. No. 14/877,920 dated Feb. 12, 2016.
Non-Final Office Action issued in U.S. Appl. No. 14/877,920 dated Apr. 22, 2016.
Final Office Action issued in U.S. Appl. No. 14/877,920 dated Aug. 30, 2016.
Notice of Allowance issued in U.S. Appl. No. 14/877,920 dated Feb. 13, 2017.
Requirement for Restriction/Election issued in U.S. Appl. No. 14/877,922 dated Jan. 12, 2016.
Non-Final Office Action issued in U.S. Appl. No. 14/877,922 dated Jun. 1, 2016.
Final Office Action issued in U.S. Appl. No. 14/877,922 dated Nov. 16, 2016.
Non-Final Office Action issued in U.S. Appl. No. 14/877,922 dated Dec. 6, 2017.
Reed et al., "Measuring Sleep Efficiency: What Should the Denominator Be?", Feb. 2016, J Clin Sleep Med 2016; 12(2): 263-266.
Walch eta., "A global quantification of "normal" sleep schedules using smartphone data", May 6, 2016, American Association for the Advancement of Science, pp. 1-6.
Requirement for Restriction/Election issued in U.S. Appl. No. 15/171,049 dated Sep. 20, 2016.
Non-Final Office Action issued in U.S. Appl. No. 15/171,049 dated Dec. 15, 2016.
Final Office Action issued in U.S. Appl. No. 15/171,049 dated Jun. 15, 2017.
Non-Final Office Action issued in U.S. Appl. No. 15/171,049 dated May 3, 2018.
Non-Final Office Action issued in U.S. Appl. No. 15/192,455 dated Nov. 30, 2016.
Final Office Action issued in U.S. Appl. No. 15/192,455 dated Jun. 21, 2017.
Non-Final Office Action issued in U.S. Appl. No. 15/192,455 dated May 14, 2018.
Non-Final Office Action issued in U.S. Appl. No. 15/199,113 dated Dec. 28, 2016.
Final Office Action issued in U.S. Appl. No. 15/199,113 dated Jul. 28, 2017.
Non-Final Office Action issued in U.S. Appl. No. 15/058,728 dated Mar. 29, 2018.
Non-Final Office Action issued in U.S. Appl. No. 15/058,986 dated Mar. 19, 2018.
Non-Final Office Action issued in U.S. Appl. No. 15/097,840 dated Jul. 25, 2017.
Notice of Allowance issued in U.S. Appl. No. 15/097,840 dated Feb. 13, 2018.
Non-Final Office Action issued in U.S. Appl. No. 14/588,848 dated Dec. 13, 2016.
Final Office Action issued in U.S. Appl. No. 14/588,848 dated Apr. 20, 2017.
Non-Final Office Action issued in U.S. Appl. No. 14/588,848 dated Jun. 6, 2017.
Notice of Allowance issued in U.S. Appl. No. 14/588,848 dated May 23, 2018.
Requirement for Restriction/Election issued in U.S. Appl. No. 14/588,853 dated Sep. 6, 2016.
Non-Final Office Action issued in U.S. Appl. No. 14/588,853 dated Jan. 13, 2017.
Final Office Action issued in U.S. Appl. No. 14/588,853 dated Feb. 17, 2017.
Non-Final Office Action issued in U.S. Appl. No. 14/588,853 dated Aug. 8, 2017.
Final Office Action issued in U.S. Appl. No. 14/588,853 dated Feb. 9, 2018.
Non-Final Office Action issued in U.S. Appl. No. 14/604,566 dated Sep. 16, 2016.
Notice of Allowance issued in U.S. Appl. No. 14/604,566 dated Nov. 30, 2016.
International Search Report and Written Opinion issued in Application No. PCT/US2017/050344 dated Mar. 16, 2018.
International Search Report and Written Opinion issued in Application No. PCT/US2017/030259 dated Apr. 29, 2016.
International Search Report and Written Opinion issued in Application No. PCT/US2015/068307 dated Jul. 7, 2016.

* cited by examiner

| | Metric | Inputs |
|---|---|---|
| Goal Driven | Total Sleep Time | User sleep goal, total sleep duration |
| | Sleep Consistency | User feedback |
| User Normalized | Restlessness | Movement, total sleep time, user N day restlessness average, standard deviation |
| | Long Wakes | Time between periods of sleep |
| | Heart Rate | Average sleep heart rate, previous day resting heart rate, heart rate pattern |
| Population Normalized | Deep Sleep (min) | Duration of deep sleep, population statistics |
| | Rapid-Eye Movement (min) | Duration of REM sleep, population statistics |
| | WASO | Time between periods of sleep, population statistics |
| | Breathing Disturbances | Duration of halted breathing, disturbed breathing thresholds |

Figure 3

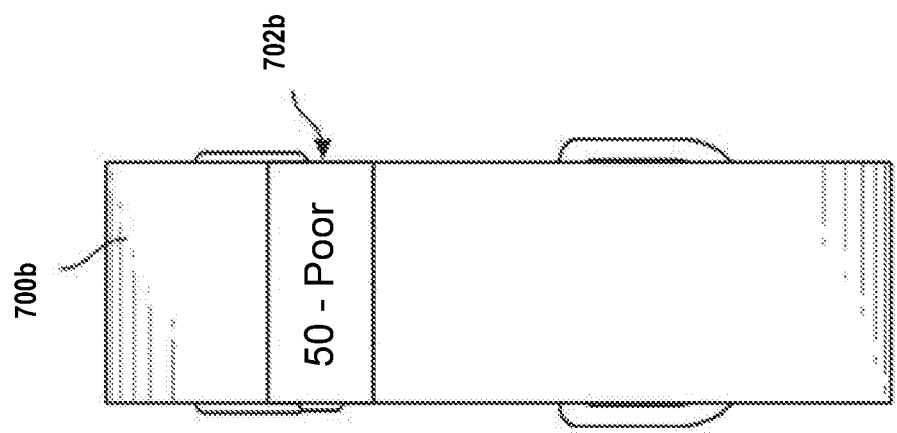
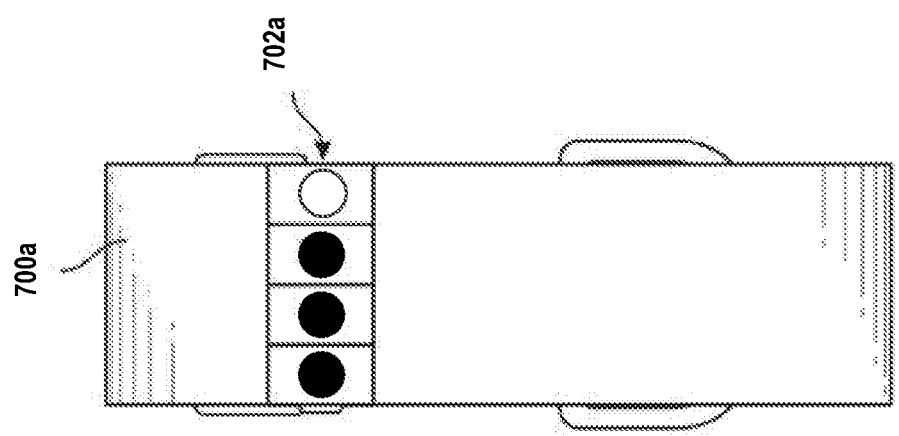
Figure 7A

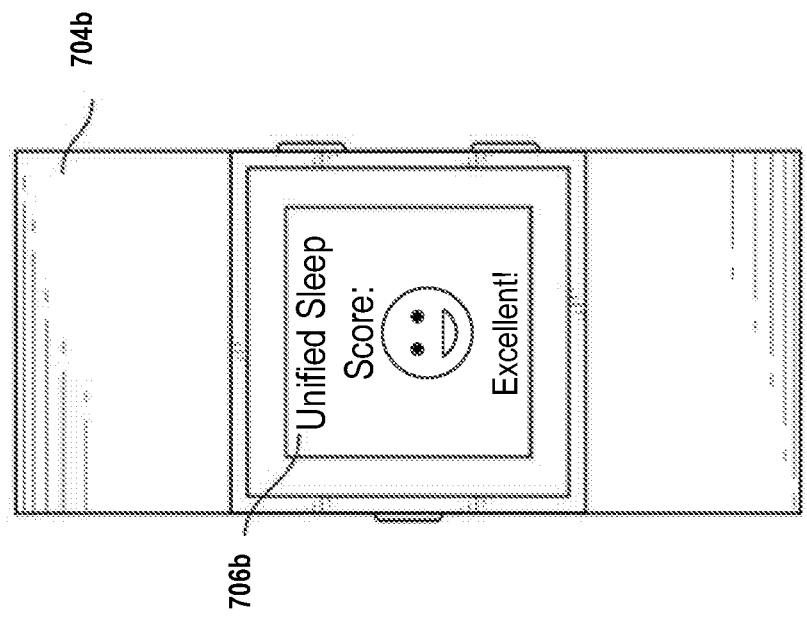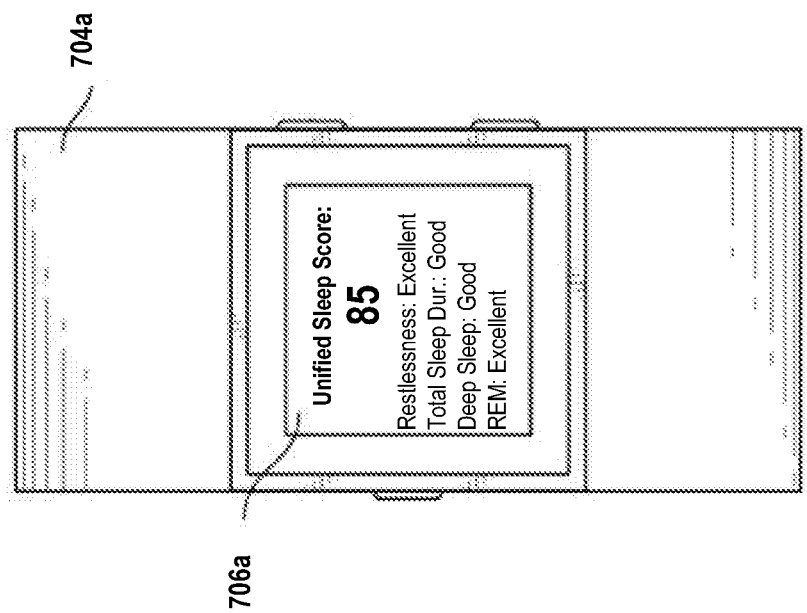
Figure 7B

SLEEP SCORING BASED ON PHYSIOLOGICAL INFORMATION

CROSS REFERENCE TO RELATED APPLICATIONS

This is a continuation application of U.S. patent application Ser. No. 15/456,494, filed on Mar. 11, 2017, entitled "SLEEP SCORING BASED ON PHYSIOLOGICAL INFORMATION," which is hereby incorporated herein by reference in its entirety.

BACKGROUND

Field

The present disclosure generally relates to the field of computing devices with one or more sensors to collect physiological information of a user.

Description of Related Art

Computing devices, such as wearable computing devices, can incorporate or interact with one or more sensors for receiving physiological information of a user, used for making health-based assessments.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 3 is a table of sleep quality assessment metrics and associated physiological data in accordance with one or more embodiments.

FIG. 7A illustrates embodiments of wearable computing devices having displays for presenting a representation of a unified sleep score in accordance with one or more embodiments.

FIG. 7B illustrates embodiments of wearable computing devices having touchscreen displays for presenting a representation of a unified sleep score in accordance with one or more embodiments.

DETAILED DESCRIPTION

Figure 1:
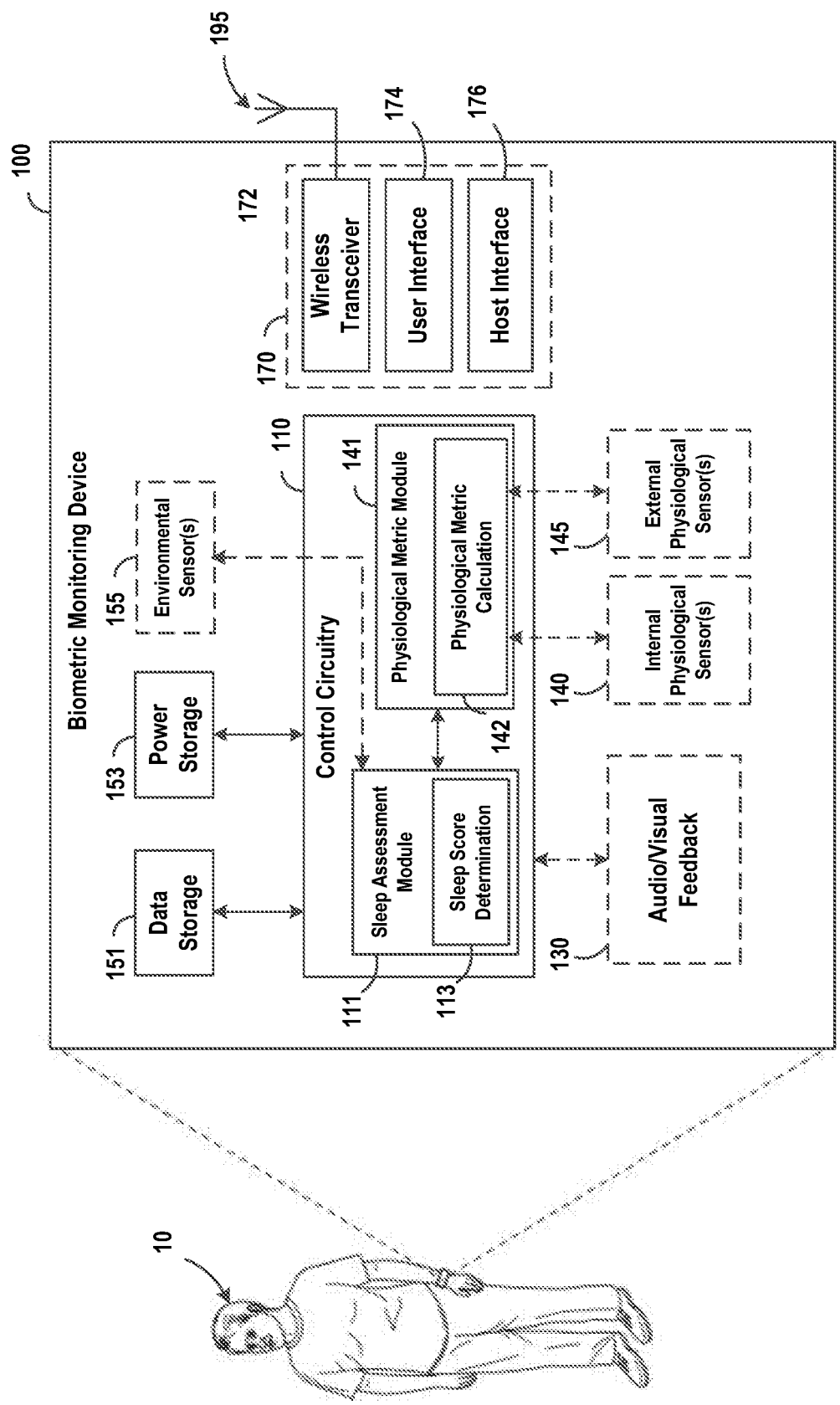
FIG. 1 is a block diagram illustrating an embodiment of a computing device in accordance with one or more embodiments.

The headings provided herein are for convenience only and do not necessarily affect the scope or meaning of the claimed invention. Like reference numbers and designations in the various drawings may or may not indicate like elements.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

As computing devices become more ubiquitous and portable, many advantages are being seen in the field of health monitoring and diagnostics. Computing devices, particularly ones that can be worn or carried by a user, may include one or more sensors to detect physiological information about the user and/or the environment around the user. This information can be used to observe, detect or diagnose various health conditions outside of a traditional clinic or laboratory setting. For example, in the context of sleep therapy, a portable or wearable electronic device may be able to detect when a user moves at night, or monitor various physiological factors such as a heart rate. Additionally, a computing device may be able to record and interpret the detected information about the user and/or environment, to determine a health assessment. As in the previous example, a wearable electronic device may be able to record a relatively high frequency of movement while the user is sleeping, and generate an assessment that the user did not have a restful period of sleep.

Assessment of sleep quality may be achieved in various ways. For example, a patient may be monitored overnight in a sleep laboratory using equipment such as electrodes and an electroencephalogram (EEG) machine. In contrast, another diagnostic technique may involve a patient performing self-assessment of nightly quality of sleep, in a journal for example. However, factors such as discomfort and unreliability pose challenges to these established techniques for sleep quality assessment. As a result, a reliable, user-friendly approach to determining sleep quality is needed. For example, by determining sleep quality of a user wearing a portable electronic device from the comfort of home, reliable physiological information can be obtained and analyzed, without the use of extensive laboratory equipment.

Certain embodiments disclosed herein provide systems, devices and methods for assessing sleep quality of a user, based on collected physiological and/or environmental data. Some embodiments implement a computing device with one or more sensors for collecting physiological data from the user and/or environmental data from the surrounding environment. For example, a portable computing device worn on the wrist of a user may include a sensor to detect a heart rate of the user, as well as a sensor to detect an external temperature. Additionally, some embodiments implement a computing device or computing system configured to use the collected physiological and/or environmental information to determine values of one or more sleep quality metrics, and to use the determined values of sleep quality metrics to create a unified sleep quality score. For example, the same portable computing device worn on the wrist of the user may determine a value of a sleep restlessness metric, and determine a unified score for sleep quality of the user, using the sleep restlessness metric value.

As described herein, in some implementations, the present disclosure is related to biometric monitoring devices. The term "biometric monitoring device" is used in the present disclosure according to its broad and ordinary meaning, and may be used in various contexts herein to refer to any type of biometric tracking devices, personal health monitoring devices, portable monitoring devices, portable biometric monitoring devices, or the like. In some embodiments, biometric monitoring devices in accordance with the present disclosure may be wearable devices, such as may be designed to be worn (e.g., continuously) by a person (i.e., "user," "wearer," etc.). When worn, such biometric monitoring devices may be configured to gather data regarding activities performed by the wearer, or regarding the wearer's physiological state. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, perspiration levels, and the like.

In some cases, a biometric monitoring device may leverage other devices external to the biometric monitoring device, such as an external heart rate monitor in the form of an EKG sensor for obtaining heart rate data, or a GPS receiver in a smartphone used to obtain position data. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

In some implementations, a method of assessing sleep quality of a user is performed at one or more electronic devices (e.g., a wearable computing device and/or a biometric monitoring device), where at least one electronic device has one or more processors, one or more physiological sensors, and memory for storing programs to be executed by the one or more processors. An electronic device may detect an initial attempt by a user to fall asleep, for example by detecting a lack of movement for a threshold period of time and/or other physiological or environmental factors such as ambient light conditions or body temperature. In some embodiments, physiological information of the user is collected or received, including at least one sleeping heart rate, such as an average heart rate since the attempt to fall asleep or a detected onset of sleep. Values for one or more sleep quality metrics may be determined, based at least in part on the collected physiological information and at least one wakeful resting heart rate of the user. For example, a wearable computing device may collect heart rate information of a user over the course of time between periods of sleep (e.g., while awake), and determine an average heart rate value for periods of relative inactivity or minimal exertion during the day (e.g., wakeful resting heart rate). Additionally, a unified score for sleep quality of the user may be determined, based at least in part on the determined sleep quality metric values.

In some implementations, the method includes presenting a representation of the unified score to the user, and/or generating this representation of the unified score. For example, a representation of the score is a number between 1 and 100, or a qualitative assessment of good, neutral or poor sleep quality.

In some implementations, the one or more sleep quality metrics includes a first set of sleep quality metrics associated with sleep quality of a plurality of users, and a second set of sleep quality metrics associated with historical sleep quality of the user. In some implementations, determining the unified score for sleep quality includes determining a respective metric-score for each of the one or more sleep quality metrics and applying a respective weighting for each of the one or more sleep quality metrics.

In some implementations, the method includes determining a wakeful resting heart rate of the user before detecting an attempt by the user to fall asleep. For example, an electronic device worn by a user periodically detects and records a heart rate (e.g., speed of a heart beat) of the user during one or more periods of time while the user is awake, and determines an average, median or another representative value for a wakeful resting heart rate.

In some implementations, collecting physiological information about the user includes collecting one or more sets of values associated with movement of the user, total sleep duration, total deep sleep duration, duration of wake time after sleep onset (WASO), total rapid-eye-movement (REM) sleep duration, total light sleep duration, breathing patterns of the user, breathing disturbances of the user and/or temperature of the user.

In some implementations, the method further includes collecting sleep quality feedback information from the user and/or receiving collected sleep quality feedback, and determining the unified score for sleep quality of the user based at least in part on the sleep quality feedback information. For example, a user may be prompted to answer one or more questions about perceived sleep quality, after waking up from a period of sleep. In this same example, the answers to the one or more questions may each be assigned a value, which is incorporated into the determination of the unified sleep score.

In some implementations, determining respective values for the one or more sleep quality metrics includes comparing the at least one sleeping heart rate of the user and the at least one resting heart rate of the user. For example, a particular user may have had an average wakeful resting heart rate of 75 beats per minute on a particular day, and an average sleeping heart rate of 45 beats per minute during the corresponding night. In this same example, if either value is relatively different from a historical average for the user, this may indicate a change in health or sleep quality.

In some implementations, the method includes detecting an onset of sleep by the user, and determining a duration of time from the attempt to fall asleep to the onset of sleep. For example, a wearable computing device may detect that the user has lain down in a darkened environment to attempt sleep at 11:05 pm, and has transitioned from wakefulness to either non-rapid eye movement (NREM) sleep or rapid-eye movement (REM) sleep at 11:15 pm.

In some implementations, the method includes detecting that the user is awake after the detected onset of sleep, and determining the respective values for one or more sleep quality metrics, in response to detecting that the user is awake. For example, detection of a user entering a state of wakefulness triggers determination of one or more sleep quality metrics, and may also trigger generation of the unified sleep quality score.

In some implementations, detecting the attempt by the user to fall asleep includes detecting contact between the device and the user. In certain embodiments, the electronic device is configured to be worn by the user. Although certain embodiments are disclosed herein in the context of a wearable electronic device worn by a user, it should be understood that detection of physiological activity and/or determination of sleep quality metrics and a unified sleep score in accordance with the present disclosure may be performed by any suitably configured electronic device, including but not limited to a computer, a server system, a smart phone, a tablet, a laptop computer, and an electronic device configured to be placed under a user during a period of sleep (e.g., a bed, pillow, blanket or mat).

In some implementations, a method of assessing sleep quality of a user is performed at one or more electronic devices, where at least one electronic device has one or more processors, one or more physiological sensors, and memory for storing programs to be executed by the one or more processors. An electronic device may detect an initial attempt by a user to fall asleep, and/or receive one or more signals indicating an attempt by a user to fall asleep, collect physiological information associated with the user and/or receive collected physiological information associated with the user, determine respective values for one or more sleep quality metrics, based at least in part on the collected physiological information, wherein the one or more sleep quality metrics includes a first set of sleep quality metrics associated with sleep quality of a plurality of users, and a second set of sleep quality metrics associated with historical sleep quality of the user, and determined a unified sleep quality score based at least in part on the values of the one or more sleep quality metrics.

In some implementations, the method includes determining the unified score for sleep quality includes using a first weighting for the first set of sleep quality metrics and a second weighting for the second set of sleep quality metrics. In some implementations, the first set of sleep quality metrics is associated with clinical sleep quality data of a demographic comparable to the user, and the second set of sleep quality metrics is associated with historical physiological information about the user for a minimum number of M days and a maximum number of N days.

In some implementations, collecting physiological information about the user includes collecting at least one sleeping heart rate and determining respective values for the one or more sleep quality metrics includes using at least one wakeful resting heart rate of the user.

The present disclosure includes certain embodiments of an electronic device comprising one or more physiological sensors, one or more processors, memory and control circuitry configured to detect an attempt by the user to fall asleep, collect physiological information about the user, including at least one sleeping heart rate, determine respective values for one or more sleep quality metrics, using the collected physiological information and at least one wakeful resting heart rate of the user and determine a unified score for sleep quality of the user, using the respective values of the one or more sleep quality metrics. Additionally, the control circuitry may be configured to perform any of the methods described herein.

The present disclosure includes certain embodiments of a non-transitory computer readable storage medium storing one or more programs, the one or more programs comprising instructions, which when executed by an electronic device with one or more physiological sensors, cause the device to detect an attempt by the user to fall asleep, collect physiological information about the user, including at least one sleeping heart rate, determine respective values for one or more sleep quality metrics, using the collected physiological information and at least one wakeful resting heart rate of the user and determine a unified score for sleep quality of the user, using the respective values of the one or more sleep quality metrics. Additionally, the non-transitory computer readable storage medium may include instructions to perform any of the methods described herein.

The present disclosure includes certain embodiments of a method of performing sleep quality assessment at a sleep quality assessment server comprising one or more processors, and memory for storing programs to be executed by the one or more processors for receiving physiological information about a user, including at least one sleeping heart rate and at least one wakeful resting heart rate of the user, determining respective values for one or more sleep quality metrics, using the collected physiological information and determining a unified score for sleep quality of the user, using the respective values of the one or more sleep quality metrics. The method may further include transmitting the unified sleep score and/or the determined values of the sleep quality metrics to a wearable computing device and/or an external computing device, such as a smart phone. Additionally, the sleep quality assessment server may be configured to perform any of the methods described herein, with respect to an electronic device and/or a server.

In some embodiments, the method includes transmitting the determined values for one or more sleep quality metrics to an electronic device. In some embodiments, the electronic device is a wearable computing device and/or the electronic device is an external computing device. In some embodiments, the electronic device has a display configured to present the unified score and/or the determined values for one or more sleep quality metrics. In some implementations, determining the unified score for sleep quality includes determining a respective metric-score for each of the one or more sleep quality metrics and using a respective weighting for each of the one or more sleep quality metrics. In some implementations, the method includes receiving sleep quality feedback information collected from the user (e.g., at a wearable computing device and/or at an external computing device), and determining the unified score for sleep quality of the user by additionally using the collected sleep quality feedback information. In some implementations, determining respective values for the one or more sleep quality metrics includes comparing the at least one sleeping heart rate of the user and the at least one wakeful resting heart rate of the user. In some implementations, the method includes receiving a trigger to determine the unified sleep quality score (e.g., receiving notice that the user is awake or has requested the score), and determining the respective values for one or more sleep quality metrics, in response to receiving the trigger to determine the unified sleep quality score. In some implementations, the method includes updating a profiles database with the received physiological information and/or the determined values of sleep quality metrics and/or the unified sleep score. In some implementations, determining respective values for one or more sleep quality metrics (e.g., of the user) includes retrieving values for one or more sleep quality metrics corresponding to a plurality of users (e.g., other users of a similar demographic to the user).

The present disclosure includes certain embodiments of a method of performing sleep quality assessment at a sleep quality assessment server comprising one or more processors, and memory for storing programs to be executed by the one or more processors for receiving physiological information about a user, determining respective values for one or more sleep quality metrics using the collected physiological information, wherein the one or more sleep quality metrics includes a first set of sleep quality metrics associated with sleep quality of a plurality of users, and a second set of sleep quality metrics associated with historical sleep quality of the user and determining a unified score for sleep quality of the user, using the respective values of the one or more sleep quality metrics. The method may further include transmitting the unified sleep score and/or the determined values of the sleep quality metrics to a wearable computing device and/or an external computing device, such as a smart phone. Additionally, the sleep quality assessment server may be configured to perform any of the methods described herein, with respect to an electronic device and/or a server.

Portable Computing Devices

Systems, devices and/or methods/processes in accordance with the present disclosure may comprise, or be implemented in connection with, a biometric monitoring device. Embodiments of the present disclosure may provide biometric monitoring devices configured to collect physiological data of a user from one or more physiological metric sensors and/or environmental data from one or more environmental sensors. Embodiments of the present disclosure may further provide biometric monitoring devices configured to analyze and interpret the collected data and/or communicate with another computing device to analyze and interpret the collected data. It is to be understood that while the concepts and discussion included herein are presented in the context of biometric monitoring devices, these concepts may also be applied in other contexts as well if the appropriate hardware is available. For example, some or all of the relevant sensor functionality may be incorporated in one or more external computing devices (e.g., smartphone) or computing systems (e.g., a server) communicatively coupled to the biometric monitoring device.

FIG. 1 is a block diagram illustrating an embodiment of a computing device 100 in accordance with one or more embodiments disclosed herein. In certain embodiments, the computing device 100 may be worn by a user 10, such as with respect to embodiments in which the computing device 100 is a wearable biometric or physiological monitoring device. For example, the computing device 100 may comprise a wearable biometric monitoring device configured to gather data regarding activities performed by the wearer, or regarding the wearer's physiological state. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, body temperature, blood oxygen levels, perspiration levels, and the like. Although certain embodiments are disclosed herein in the context of wearable biometric monitoring devices, it should be understood that biometric/physiological monitoring and health assessment principles and features disclosed herein may be applicable with respect to any suitable or desirable type of computing device or combination of computing devices, whether wearable or not.

The computing device 100 may include one or more audio and/or visual feedback modules 130, such as electronic touchscreen display units, light-emitting diode (LED) display units, audio speakers, LED lights or buzzers. In certain embodiments, the one or more audio and/or visual feedback modules 130 may be associated with the front side of the computing device 100. For example, in wearable embodiments of the computing device 100, an electronic display may be configured to be externally presented to a user viewing the computing device 100.

The computing device 100 includes control circuitry 110. Although certain modules and/or components are illustrated as part of the control circuitry 110 in the diagram of FIG. 1, it should be understood that control circuitry associated with the computing device 100 and/or other components or devices in accordance with the present disclosure may include additional components and/or circuitry, such as one or more of the additional illustrated components of FIG. 1. Furthermore, in certain embodiments, one or more of the illustrated components of the control circuitry 110 may be omitted and/or different than that shown in FIG. 1 and described in association therewith. The term "control circuitry" is used herein according to its broad and/or ordinary meaning, and may include any combination of software and/or hardware elements, devices or features, which may be implemented in connection with operation of the computing device 100. Furthermore, the term "control circuitry" may be used substantially interchangeably in certain contexts herein with one or more of the terms "controller," "integrated circuit," "IC," "application-specific integrated circuit," "ASIC," "controller chip," or the like.

The control circuitry 110 may comprise one or more processors, data storage devices, and/or electrical connections. For example, the control circuitry 110 may comprise one or more processors configured to execute operational code for the computing device 100, such as firmware or the like, wherein such code may be stored in one or more data storage devices of the computing device 100. In one embodiment, the control circuitry 110 is implemented on an SoC (system on a chip), though those skilled in the art will recognize that other hardware/firmware implementations are possible.

The control circuitry 110 may comprise a sleep quality assessment module 113. The sleep quality assessment module 113 may comprise one or more hardware and/or software components or features configured to make an assessment of sleep quality of a user, optionally using inputs from one or more environmental sensors 155 (e.g., ambient light sensor) and information from the physiological metric module 141. In certain embodiments, the sleep assessment module 111 includes a sleep score determination module 113 configured to determine a unified sleep quality score, using information accumulated by the sleep assessment module 111, such as the values of one or more physiological metrics determined by the physiological metric calculation module 142 of the physiological metric module 141. In certain embodiments, the physiological metric module 141 is optionally in communication with one or more internal physiological sensors 140 embedded or integrated in the biometric monitoring device 100. In certain embodiments, the physiological metric module 141 is optionally in communication with one or more external physiological sensors 145 not embedded or integrated in the biometric monitoring device 100 (e.g., an electrode, or sensor integrated in another electronic device). Examples of internal physiological sensors 140 and external physiological sensors 145 include, but are not limited to, sensors for measuring body temperature, heart rate, blood oxygen level and movement.

The computing device may further comprise one or more data storage modules 151, which may include any suitable or desirable type of data storage, such as solid-state memory, which may be volatile or non-volatile. Solid-state memory of the computing device 100 may comprise any of a wide variety of technologies, such as flash integrated circuits, Phase Change Memory (PC-RAM or PRAM), Programmable Metallization Cell RAM (PMC-RAM or PMCm), Ovonic Unified Memory (OUM), Resistance RAM (RRAM), NAND memory, NOR memory, EEPROM, Ferroelectric Memory (FeRAM), MRAM, or other discrete NVM (non-volatile solid-state memory) chips. The data storage 151 may be used to store system data, such as operating system data and/or system configurations or parameters. The computing device 100 may further comprise data storage utilized as a buffer and/or cash memory for operational use by the control circuitry 110.

Data storage modules 151 may include various sub-modules, including, but not limited to one or more of a sleep detection module for detecting an attempt or onset of sleep by the user 10, an information collection module for managing the collection of physiological and/or environmental data relevant to a sleep quality assessment, a sleep quality metric calculation module for determining values of one or more sleep quality metrics as described in the present disclosure, a unified score determination module for determining a representation of a unified sleep quality score as described in the present disclosure, a presentation module for managing presentation of sleep quality assessment information to user 10, a heart rate determination module for determining values and patterns of one or more types of heart rates of user 10, a feedback management module for collecting and interpreting sleep quality feedback from user 10.

The computing device 100 further comprises power storage 153, which may comprise a rechargeable battery, one or more capacitors, or other charge-holding device(s). The power stored by the power storage module 153 maybe utilized by the control circuitry 110 for operation of the computing device 100, such as for powering the touchscreen display 130. The power storage module 153 may receive power over the host interface 176 or through other means.

The computing device 100 may comprise one or more environmental sensors 155. Examples of such environmental sensors 155 include, but are not limited to sensors for measuring ambient light, external (non-body) temperature, altitude and global-positioning system (GPS) data.

The computing device 100 may further comprise one or more connectivity components 170, which may include, for example, a wireless transceiver 172. The wireless transceiver 172 may be communicatively coupled to one or more antenna devices 195, which may be configured to wirelessly transmit/receive data and/or power signals to/from the computing device using, but not limited to peer-to-peer, WLAN or cellular communications. For example, the wireless transceiver 172 maybe utilized to communicate data and/or power between the computing device 100 and an external host system (not shown), which may be configured to interface with the computing device 100. In certain embodiments, the computing device 100 may comprise additional host interface circuitry and/or components 176, such as wired interface components for communicatively coupling with a host device or system to receive data and/or power therefrom and/or transmit data thereto.

The connectivity circuitry 170 may further comprise user interface components 174 for receiving user input. For example, the user interface 174 may be associated with one or more audio/visual feedback modules 130, wherein the touchscreen display is configured to receive user input from user contact therewith. The user interface module 174 may further comprise one or more buttons or other input components or features.

The connectivity circuitry 170 may further comprise the host interface 176, which may be, for example, an interface for communicating with a host device or system (not shown) over a wired or wireless connection. The host interface 176 may be associated with any suitable or desirable communication protocol and/or physical connector, such as Universal Serial Bus (USB), Micro-USB, WiFi, Bluetooth, FireWire, PCIe, or the like. For wireless connections, the host interface 176 may be incorporated with the wireless transceiver 172.

Although certain functional modules and components are illustrated and described herein, it should be understood that authentication management functionality in accordance with the present disclosure may be implemented using a number of different approaches. For example, in some implementations the control circuitry 110 may comprise one or more processors controlled by computer-executable instructions stored in memory so as to provide functionality such as is described herein. In other implementations, such functionality may be provided in the form of one or more specially-designed electrical circuits. In some implementations, such functionality may be provided by one or more processors controlled by computer-executable instructions stored in a memory coupled with one or more specially-designed electrical circuits. Various examples of hardware that may be used to implement the concepts outlined herein include, but are not limited to, application specific integrated circuits (ASICs), field-programmable gate arrays (FPGAs), and general-purpose microprocessors coupled with memory that stores executable instructions for controlling the general-purpose microprocessors.

Wearable Computing Devices

In some implementations, a portable computing device, such as computing device 100 of FIG. 1, may be designed so that it can be inserted into a wearable case or into one or more of multiple different wearable cases (e.g., a wristband case, a belt-clip case, a pendant case, a case configured to be attached to a piece of exercise equipment such as a bicycle, etc.). In other implementations, a portable computing device may be designed to be worn in limited manners, such as a computing device that is integrated into a wristband in a non-removable manner, and may be intended to be worn specifically on a person's wrist (or perhaps ankle). Irrespective of configuration, wearable computing devices having one or more physiological and/or environmental sensors may be configured to collect physiological and/or environmental data in accordance with various embodiments disclosed herein. Wearable computing devices may also be configured to analyze and interpret collected physiological and/or environmental data to perform a sleep quality assessment of a user (e.g., wearer) of the computing device, or may be configured to communicate with another computing device or server that performs the sleep quality assessment.

Figure 2A:
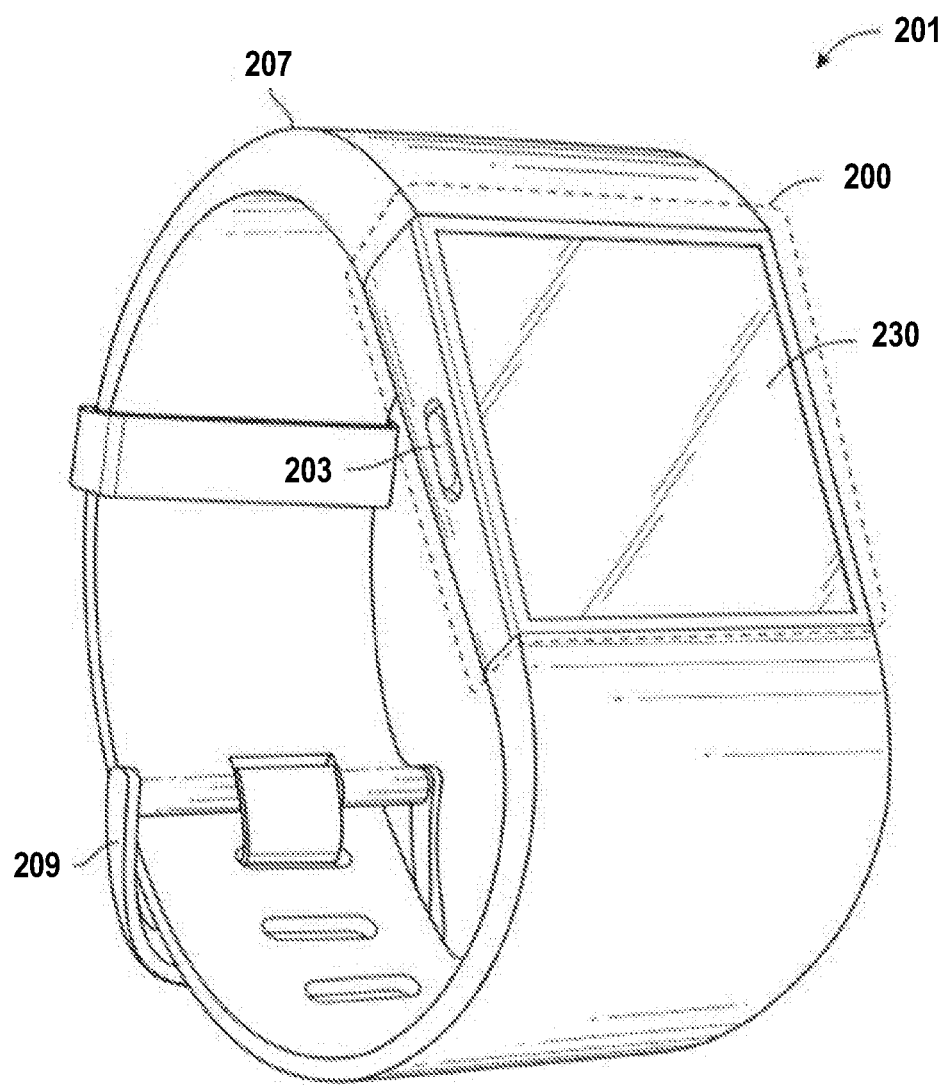
FIG. 2A shows perspective front and side views of a wearable computing device in accordance with one or more embodiments.

Wearable computing devices according to embodiments and implementations described herein may have shapes and sizes adapted for coupling to (e.g., secured to, worn, borne by, etc.) the body or clothing of a user. An example of a wearable computing device 201 is shown in FIG. 2A. FIG. 2A shows perspective front and side views of the wearable computing device 201. The wearable computing device 201 includes both a computing device 200, as well as a band portion 207. In certain embodiments, the band portion 207 includes first and second portions that may be connected by a clasp portion 209. The computing device portion 200 may be insertable, and may have any suitable or desirable dimensions. Wearable computing devices may generally be relatively small in size so as to be unobtrusive for the wearer, and therefore, an optional touchscreen display 230 may be relatively small in size relative to certain other computing devices. The computing device 200 may be designed to be able to be worn without discomfort for long periods of time and to not interfere with normal daily activity or with sleep.

The electronic display 230 may comprise any type of electronic display known in the art. For example, the display 230 may be a liquid crystal display (LCD) or organic light emitting diode (OLED) display, such as a transmissive LCD or OLED display. The electronic display 230 may be configured to provide brightness, contrast, and/or color saturation features according to display settings maintained by control circuitry and/or other internal components/circuitry of the computing device 200.

The touchscreen 230 may be a capacitive touchscreen, such as a surface capacitive touchscreen or a projective capacitive touch screen, which may be configured to respond to contact with electrical charge-holding members or tools, such as a human finger.

Wearable computing devices, such as biometric monitoring devices, in accordance with the present disclosure may incorporate one or more existing functional components or modules designed for determining one or more physiological metrics associated with a user (e.g., wearer) of the device, such as a heart rate sensor (e.g., photoplethysmograph sensor), body temperature sensor, environment temperature sensor or the like. Such components/modules may be disposed or associated with an underside/backside of the biometric monitoring device, and may be in contact or substantially in contact with human skin when the biometric monitoring device is worn by a user. For example, where the biometric monitoring device is worn on the user's wrist, the physiological metric component(s)/module(s) may be associated with an underside/backside of the device substantially opposite the display and touching the arm of the user.

In one embodiment, the physiological and/or environmental sensors (sources and/or detectors) may be disposed on an interior or skin-side of the wearable computing device (i.e., a side of the computing device that contacts, touches, and/or faces the skin of the user (hereinafter "skin-side"). In another embodiment, the physiological and/or environmental sensors may be disposed on one or more sides of the device, including the skin-side and one or more sides of the device that face or are exposed to the ambient environment (environmental side).

Figure 2B:
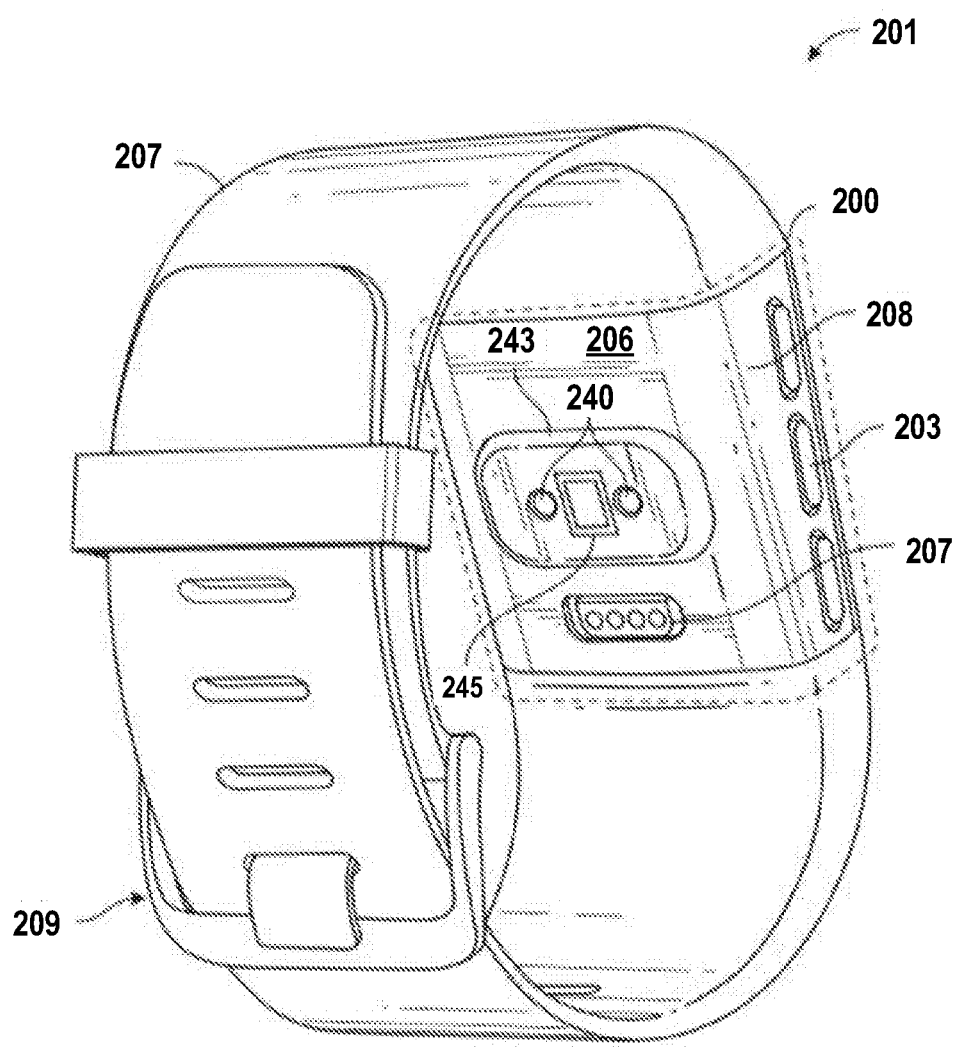
FIG. 2B shows perspective back and side views of a wearable computing device in accordance with one or more embodiments.

FIG. 2B is a perspective back and side view of the wearable biometric monitoring device 201 of FIG. 2A. The wearable biometric monitoring device 201 comprises a band portion 207, which may be configured to be latched or secured about a user's arm or other appendage via a securement mechanism of any suitable or desirable type. For example, the band 207 may be secured using a hook and loop clasp component 209. In certain embodiments, the band 207 is designed with shape memory to promote wrapping around the user's arm.

The wearable biometric monitoring device 201 includes a biometric monitoring device component 200, which may be at least partially secured to the band 207. The view of FIG. 2B shows a backside 206 (also referred to herein as the "underside") of the biometric monitoring device 200, which may generally face and/or contact skin or clothing associated with the user's arm, for example. The terms "backside" and "underside" are used herein according to their broad and ordinary meaning, and may be used in certain contexts to refer to a side, panel, region, component, portion and/or surface of a biometric monitoring device that is positioned and/or disposed substantially opposite to a user display screen, whether exposed externally of the device, or at least partially internal to an electronics package or housing of the device.

The wearable biometric monitoring device 201 may include one or more buttons 203, which may provide a mechanism for user input. The wearable biometric monitoring device 201 may further comprise a device housing, which may comprise one or more of steel, aluminum, plastic, and/or other rigid structure. The housing 208 may serve to protect the biometric monitoring device 200 and/or internal electronics/components associated therewith from physical damage and/or debris. In certain embodiments, the housing 208 is at least partially waterproof.

The backside 206 of the biometric monitoring device 200 may have an optical physiological metric sensor 243 associated therewith, which may comprise one or more sensor components, such as one or more light sources 240 and/or light detectors 245, the collection of which may represent an example of an internal physiological metric sensor 140 of FIG. 1. In certain embodiments, the optical physiological metric sensor 243 comprises a protrusion form protruding from the back surface of the biometric monitoring device 200. The sensor components may be used to determine one or more physiological metrics of a user wearing the wearable biometric monitoring device 201. For example, the optical physiological sensor components associated with the sensor 243 may be configured to provide readings used to determine heart rate (e.g., in beats-per-minute (BPM)), blood oxygenation (e.g., $SpO_2$), blood pressure, or other metric. In certain embodiments, the biometric monitoring device 200 further includes an electrical charger mating recess 207.

Although the sensor 243 is illustrated as comprising a protrusion from certain figures herein, it should be understood that backside sensor modules in accordance with the present disclosure may or may not be associated with a protrusion form. In certain embodiments, the protrusion form on the backside of the device may be designed to engage the skin of the user with more force than the surrounding device body. In certain embodiments, an optical window or light-transmissive structure may be incorporated in a portion of the protrusion 243. The light emitter(s) 240 and/or detector(s) 245 of the sensor module 243 may be disposed or arranged in the protrusion 243 near the window or light-transmissive structure. As such, when attached to the user's body, the window portion of the protrusion 243 of the biometric monitoring device 200 may engage the user's skin with more force than the surrounding device body, thereby providing a more secure physical coupling between the user's skin and the optical window. That is, the protrusion 243 may cause sustained contact between the biometric monitoring device and the user's skin that may reduce the amount of stray light measured by the photodetector 245, decrease relative motion between the biometric monitoring device 200 and the user, and/or provide improved local pressure to the user's skin, some or all of which may increase the quality of the cardiac signal of interest generated by the sensor module. Notably, the protrusion 243 may contain other sensors that benefit from close proximity and/or secure contact to the user's skin. These may be included in addition to or in lieu of a heart rate sensor and may include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

Collecting Physiological and/or Environmental Information

The wearable computing device 201 may be configured to collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing the wearable computing device 201, the wearable computing device 201 may calculate and store the user's step count using one or more biometric sensors. The wearable computing device 201 may then transmit data representative of the user's step count to an account on a web service, computer, mobile phone, or health station where the data may be stored, processed, and visualized by the user. Indeed, the wearable computing device 201 may measure or calculate a plurality of other physiological metrics in addition to, or in place of, the user's step count. These include, but are not limited to, energy expenditure, e.g., calorie burn, floors climbed and/or descended, heart rate, heart rate variability, heart rate recovery, location and/or heading, e.g., through GPS or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics.

The wearable computing device 201 may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the wearable computing device 201 or the system collating the data streams from the wearable computing device 201 may calculate metrics derived from such data. For example, the device or system may calculate the user's stress and/or relaxation levels through a combination of heart rate variability, skin conduction, noise pollution, and body temperature. Similarly, the wearable computing device 201 or the system collating the data streams from the wearable computing device 201 may determine values corresponding to sleep quality metrics derived from such data. For example, the device or system may calculate the user's restlessness and/or quality of rapid-eye movement (REM) sleep through a combination of heart rate variability, blood oxygen level, sleep duration, and body temperature. In another example, the wearable computing device 201 may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. Pat. No. 9,167,991, titled "Portable Biometric Monitoring Devices and Methods of Operating Same" filed Jun. 8, 2011, which is hereby incorporated herein by reference in its entirety.

Sleep Quality Metrics

As described above, a reliable, yet user-friendly approach is desired in the field of sleep therapy and sleep quality assessment. FIG. 3 is a table 300 of sleep quality assessment metrics and associated physiological data in accordance with one or more embodiments of the present disclosure. Table 300 includes a metric column 302 and input column 304 as well as three rows of types of sleep quality metrics, namely user goal-driven metrics 306, user-normalized metrics 308 and population-normalized metrics 310. In some embodiments, inputs in input column 304 include directly detected physiological and/or environmental sensor readings (e.g., instantaneous heart rate), while in some embodiments, inputs in input column 304 include intermediate parameters derived from directly detected physiological and/or environmental sensor readings (e.g., average heart rate over a period of sleep). Further embodiments and implementations of collecting and interpreting physiological and/or environmental sensor readings for sleep quality assessment may be found in U.S. patent application Ser. No. 15/438,643, titled "Methods and Systems for Labeling Sleep States" filed Feb. 21, 2017, which is hereby incorporated herein by reference in its entirety.

The various sleep quality metrics conveyed in table 300 are each associated with a distinct diagnostic basis for sleep quality. For example, one aspect of good sleep health is having an adequate total duration of sleep corresponding to the age, gender and overall health of a respective user. The first type of sleep quality metric that may be used to determine a unified sleep score, is goal-driven 306. Goal-driven metrics 306 may require input from a user to set one or more sleep goals, and may require feedback from a user regarding perceived quality of sleep. Goal-driven metrics 306, include, but are not limited to, a total sleep time metric and a sleep consistency metric.

Determining a value for the total sleep time metric may rely on one or more inputs, including, but not limited to a user-specified minimum target duration of sleep goal, a maximum target duration of sleep goal and/or a target range of sleep goal. For example, a biometric monitoring device performing a sleep quality assessment, may prompt a user to enter a goal for achieving a duration of sleep for a given night (e.g., sleep for at least 7 hours tonight), or to enter a goal for achieving a duration of sleep every night (e.g., sleep for 7-8 hours every night). Determining a value for the total sleep time metric may also rely on a determined value of total sleep duration achieved by the user for a respective period of sleep. For example, a wearable computing device may detect that a user fell asleep at 11 PM on Monday night, and woke up at 6 AM on Tuesday morning, for a total sleep duration of 7 hours. In some embodiments, the onset of sleep and the onset of wakefulness are detected by one or more physiological sensors. Determining a value for the total sleep time metric may use the user-specified sleep goal along with the detected total sleep duration for a respective period of sleep (e.g., for a given night), and generate a value corresponding to a level of achievement for reaching the user-specified goal. For example, if the user aimed to sleep for at least 7 hours, and had a total sleep duration for 7.5 hours, the total sleep time metric would have a maximum value (e.g., 10 out of 10 or 100%) for a given range of possible values.

Another of the possible goal-driven metrics 306, is sleep consistency. In some implementations, a value of a sleep consistency metric relies on feedback obtained from a user after waking from a period of sleep. For example, a biometric monitoring device may detect that a user has awoken from a night of sleep and prompt the user to provide a self-assessment of perceived quality of sleep or feeling of restfulness. This feedback may be in a numerical format (e.g., 7 out of 10) or a subjective form, which is converted into a numerical value (e.g., good=1, neutral=0, bad=−1).

The second type of sleep quality metric that may be used to determine a unified sleep score, is user-normalized 308. User-normalized metrics 308 are specific to a respective user undergoing sleep assessment, and rely on historical physiological information about the user. In certain embodiments, determining a respective value for a respective user-normalized metric 308 may require at least M days worth of detected physiological and/or environmental data (e.g., at least 7 days). In some embodiments, determining a respective value of a respective user-normalized metric 308 may use up to a maximum N days worth of the most recently detected physiological and/or environmental data (e.g., at most the last 30 days). User-normalized metrics 308 may include, but not be limited to, a restlessness metric, a long wakes metric and a heart rate metric.

In some implementations, a value of a restlessness metric is determined using a value for detected movement of a user during a period of sleep. A degree of movement may be based on a duration of detected movement while a user is asleep. For example, a computing device worn by a user while asleep detects that the user remained nearly motionless for 6 out of 7 hours of sleep, which may indicate a low degree of movement during the period of sleep. A degree of movement may be based on a severity of detected movement while a user is asleep. For example, if a user has a bad dream and moves with great force or great speed, this movement may indicate a high degree of movement during the period of sleep. A value of a restlessness metric may also rely on a value of detected total sleep duration. For example, if 15 minutes of movement were detected during an 8 hour period of sleep, this would indicate less overall restlessness than detecting 15 minutes of movement during a 5 hour period of sleep. A value or weighting of the value of the restlessness metric may also involve comparing a current assessment of restlessness to the user's historical values of the restlessness metric. For example, if the user typically has a relatively calm night of sleep with little movement, a night with a high restlessness score has a relatively high standard deviation from the normal values and may be weighted more negatively than if the user typically has restless sleep. Similarly, in this same example, if the user typically has a restless night of sleep, a night with a low restlessness score may be weighted more positively than for a user who typically has calm nights of sleep.

In some implementations, a value of a long wakes metric is determined using a value representing a detected period of wakefulness or total duration of time between periods of sleep. For example, if a user gets up out of bed multiple times in a given night, the value of the long wakes metric may be low, indicating that the user did not have a long, continuous period of sleep. Similarly to the restlessness metric, determining the value or a weighting of the value of the long wakes metric may involve comparing the value of the determined long wakes metric to historical values of the long wakes metric for a respective user.

In some implementations, a value of a heart rate metric is determined using one or more heart rate parameters. Determining a value for the heart rate metric may include using a value representing the average heart rate of a user during a period of sleep (e.g., 45 beats per minute). For example, if the user had an average sleeping heart rate above a particular threshold (e.g., 60 beats per minute), this may result in a low value for the heart rate metric. The average sleeping heart rate of a user may also be compared to historical average sleeping heart rates of the user for a number of days, to assess if the currently determined average sleeping heart rate is abnormally high or low for the user.

In some implementations, the value of a heart rate metric includes assessment of a wakeful resting heart rate of the user during a long duration of wakefulness before detecting that the user is attempting to sleep (e.g., during the day before a night's sleep). For example, a user may have had an average resting heart rate of 55 beats per minute during the day, and an average sleeping heart rate of 53 beats per minute. This unusually small difference between the average resting heart rate of the user during the day and the average sleeping heart rate of the user while asleep may result in a low value for the heart rate metric, indicating that the user may not have had a good night of sleep. In some implementations, detection of a sleeping heart rate (e.g., average, median, or instantaneous) value above a wakeful resting heart rate value is an indication of poor quality sleep. As a result, the heart rate metric may be assigned a low value and/or the weight of the heart rate metric value in determining a population-normalized score and/or the unified sleep score may be increased.

The use of a wakeful resting heart rate of the user may also indicate a mental or physical health condition (e.g., a cold, or anxiety), which may affect detected and/or perceived sleep quality. For example, if a user has a relatively high resting heart rate for several days or weeks in a row, this may correspond to a relatively high sleeping heart rate for the same several days or weeks. As a result, weighting of the value of an average sleeping heart rate may be lessened to compensate for this change in physical and/or mental health of the user. While the examples of a detected heart rate have referred to averaged values, in some implementations another statistical basis may be used to assess a respective heart rate of a user. For example, an entire heart rate pattern may be analyzed for a given period of time (e.g., total duration of sleep). A median heart rate value may be used instead of an average heart rate value for a given heart rate parameter. Extreme values for heart rates over a period of time may also be filtered out before performing a statistical operation to determine a representative value for a respective type of heart rate.

The third type of sleep quality metric that may be used to determine a unified sleep score, is population-normalized 310. Population-normalized metrics 308 are sleep quality metrics assessed with respect to a plurality of users. In certain embodiments, determining a respective value for a respective population-normalized metric 310 includes comparing determined values for a user to those of other users of a similar demographic (e.g., same gender, same age range, same occupation). Population-normalized metrics 310 may include, but not be limited to, a deep sleep metric, a rapid-eye movement (REM) metric, a wake after sleep onset (WASO) metric and a breathing disturbances metric. Population-normalized metrics may be associated with a plurality of users of the sleep quality assessment system described herein, and/or with clinical data obtained from sleep therapy resources such as sleep laboratory readings of various patients.

In some implementations, a value of a deep sleep metric is determined using a determined value of a duration of time that a user experiences deep sleep during a total duration of sleep. In some embodiments, a total duration of non-rapid eye movement (NREM) sleep is used for determining the value of the deep sleep metric, while in some embodiments, a total duration of deep sleep is a subset of time during a total duration of NREM sleep. For example, a total duration of deep sleep is determined to include time when brain waves of a user have a frequency of less than 1 Hz. Deep sleep is physiologically linked to the consolidation of new memories, and physical and mental recovery. As a result, a relatively low value of duration of deep sleep, as compared to a plurality of users, may result in a low value for the deep sleep metric.

In some implementations, a value of a rapid-eye movement (REM) sleep metric is determined using a value of a duration of time that a user experiences REM sleep during a total duration of sleep. In some implementations, duration of REM sleep and/or NREM sleep and/or deep sleep is determined on the basis of detected movement of a user, heart rate, breathing patterns, brain activity and/or body temperature. REM sleep deprivation is linked to mental and physical health issues, therefore a relatively low value of duration of REM sleep, as compared to a plurality of users, may result in a low value for the REM sleep metric.

In some implementations, a value of a wake after sleep onset (WASO) metric is determined using a value of total or average time between periods of sleep that a user experiences during a total duration of sleep. For example, a user may wake up three times at night due to nightmares or environmental disturbances, and have a total value of 45 minutes of time between periods of sleep. Continuous sleep is linked to improvements in duration of REM and deep sleep, therefore, a relatively high value of total or average time between periods of sleep as compared to a plurality of users, may result in a low value for a WASO metric.

In some implementations, a value of a breathing disturbances metric is determined using a value of a detected duration of halted breathing that a user experiences during a total duration of sleep. For example, a wearable computing device worn by a user while asleep, may detect a pulse oximeter reading below 90%, indicating a low blood oxygen level and suggesting that the user has stopped breathing. In this example, the user may wake up, start breathing again, and have a pulse oximeter reading greater than 90% or another threshold value for some time. While a pulse oximeter is one example of a physiological sensor to determine breathing disturbances, measurement of a duration of halted breathing by a user during sleep, is not limited to this example. Duration of halted breathing may also be detected by brain activity, for example. Threshold levels of blood oxygen levels, brain activity and/or breathing activity for determining a high level of breathing disturbances, may be determined by a plurality of users.

While table 300 portrays several sleep quality metrics and several types of sleep quality metrics that may be utilized by a biometric monitoring device to determined a unified sleep quality score, it should be understood that additional sleep quality metrics may be used. Furthermore, in some implementations a subset of the sleep quality metrics shown in table 300 are used to determined a sleep quality score. For example, a wearable computing device that does not have a sensor to determine breathing disturbances does not use the breathing disturbances metric to determine a unified sleep quality score for purposes of sleep quality assessment.

Generation of Unified Sleep Quality Score

Figures 4A, 4B:
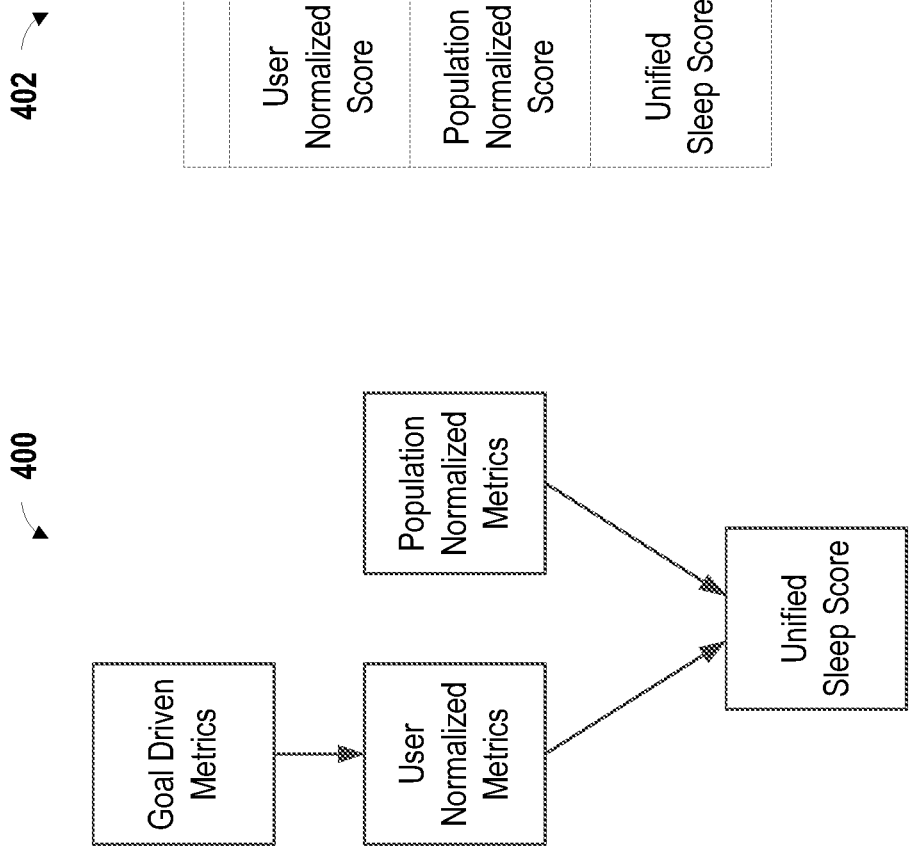
FIG. 4A is a block diagram of a basis of determining a unified sleep score in accordance with one or more embodiments.
FIG. 4B is a table of a basis of determining a unified sleep score in accordance with one or more embodiments.

FIG. 4A is a block diagram 400 of a basis of determining a unified sleep score in accordance with one or more embodiments. In some implementations, one or more goal-driven metrics are used along with one or more user normalized metrics, each as described above with respect to FIG. 3, to determine an overall user normalized score. In some implementations, goal-driven metrics are not used to determine an overall user normalized score. In some implementations, population normalized metrics, as described above with respect to FIG. 3, are used to determine an overall population normalized score.

The determination of the user normalized score and the population normalized score depends on which specific sleep quality metrics are used and the weight of each selected sleep quality metric in the calculation of the each score. For example, a total sleep time, goal-driven sleep quality metric, may be given a relatively high weight in determining the user normalized score, while a restlessness metric may be given a relatively low weight, or determined not to be used. In some implementations, the selection of sleep metrics used to determine the user normalized and/or population normalized score depends on the capability of a biometric monitoring device used to perform sleep assessment of a user. For example, if a user wears a computing device that cannot measure a heart rate, the heart rate metric is not used to determine the user normalized score.

The weighting basis for sleep metrics used to determine the user normalized score and/or the population normalized score may change automatically or manually. For example, an atypical value for a respective sleep quality metric may result in a higher than default weighting for that respective sleep quality metric, or may limit the upper or lower bound of an associated score. The weighting basis may also change over time as a user develops better sleep habits, in order to motivate the user to continually achieve better sleep quality. The weighting basis may adjust from a default basis after a period of collecting physiological and/or environmental data while a user sleeps for a minimum threshold number of total sleep periods (e.g., nights). A user may also be able to adjust the weighting basis for one or more sleep quality metrics, in determining an overall unified sleep quality score, which relies on the various goal-driven, user normalized and/or population normalized metrics. For example, a user may be able to indicate a strong link to restlessness and perceived sleep quality, resulting in an increased weighting of that metric. In some implementations, one or more population-normalized metrics are given more weight than one or more user-normalized metrics, while in some implementations one or more user-normalized metrics are given more weight than one or more population-normalized metrics.

After determining a respective user normalized score and a respective population normalized score for sleep quality, a unified sleep quality score is determined, using the user normalized score and the population normalized score. In some implementations, there is a weighting component of each of the user normalized score and the population normalized score in the determination of the unified sleep score. This weighting component may be adjusted manually or automatically, as described above with respect to the weighting basis for each of the user normalized and population normalized scores.

FIG. 4B is a table 402 of a basis of determining a unified sleep score in accordance with one or more embodiments. The examples of table 402 are non-limiting, and are merely used to illustrate one particular technique for using a user normalized score and a population normalized score to generate a unified sleep quality score. As described with respect to FIGS. 3 and 4A, a user normalized score may be based on one or more of a heart rate metric, a total sleep time metric, a sleep consistency metric, a restlessness metric, and a time between sleep periods metric. It should be understood that this is a non-limiting scoring basis for generating the user normalized score, and that a user normalized score may be based on additional user-specific sleep quality metrics not described herein. As described with respect to FIGS. 3 and 4A, a population normalized score may be based on one or more of a deep sleep metric, a REM metric, a WASO metric and a breathing disturbances metric. It should be understood that this is a non-limiting scoring basis for generating the population normalized score, and that a population normalized score may be based on additional population normalized sleep quality metrics not described herein.

A user normalized score may be determined and converted into a numerical value on a preset scale (e.g., −4 to 1, or 0 to 4, or 1 to 100). Similarly, a population normalized score may be determined and converted into a numerical value on a preset scale. The non-limiting examples shown in table 402 illustrate a range of values from −4 at the worst to 1 at the best for a user normalized score, and from −1 at the worst to 1 at the best for a population normalized score. In some embodiments, the user normalized score and the population normalized score use the same scoring value range. The non-limiting example calculation of a unified sleep quality score combines the determined user normalized score and population normalized score, multiplies the sum by 10, and adds the result to 80 to obtain a final value ranging from 30 at the worst to 100 at the best.

Sleep Quality Assessment System

Figure 5:
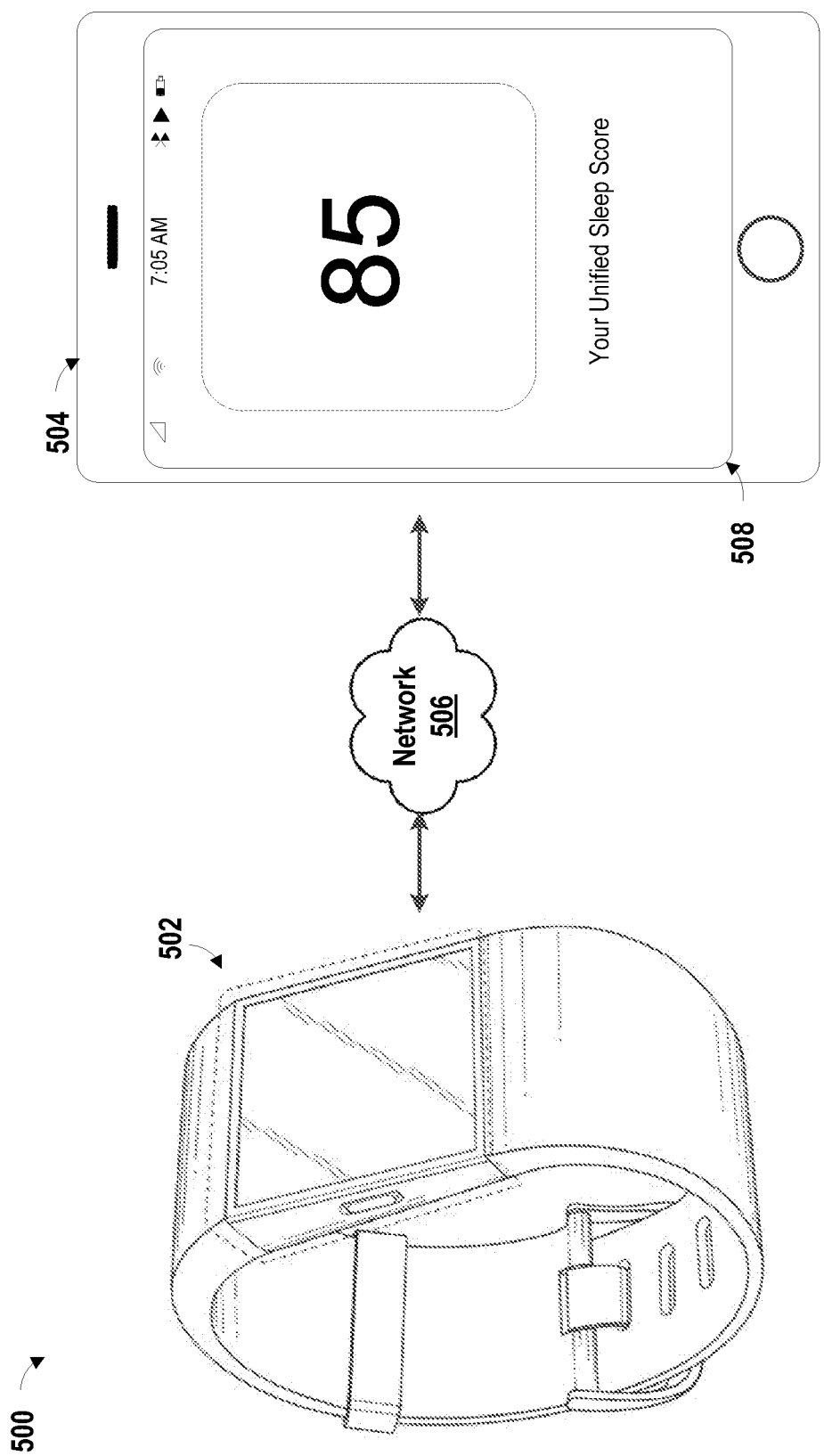
FIG. 5 illustrates a networked relationship between a wearable computing device and an external computing device in accordance with one or more embodiments.

In certain embodiments described in the present disclosure, a wearable computing device is capable of, and configured to collect physiological sensor readings of a user, and determine values of one or more sleep quality metrics and/or a unified sleep score. However, in some embodiments, a wearable computing device, or another portable electronic device used to detect physiological information of a user, is in communication with another computing device configured to determine these values. FIG. 5 illustrates a networked relationship 500 between a wearable computing device 502 and an external computing device 504 in accordance with one or more embodiments.

The wearable computing device 502 may be configured to collect one or more types of physiological and/or environmental data from embedded sensors and/or external devices, as described throughout the present disclosure, and communicate or relay such information over one or more networks 506 to other devices. This includes, in some implementations, relaying information to devices capable of serving as Internet-accessible data sources, thus permitting the collected data to be viewed, for example, using a web browser or network-based application at an external computing device 504. For example, while the user is asleep and wearing the wearable computing device 502, the wearable computing device 502 may calculate and optionally store the user's sleeping heart rate using one or more biometric sensors. The wearable computing device 502 may then transmit data representative of the user's sleeping heart rate over network 506 to an account on a web service, computer, mobile phone, or health station where the data may be stored, processed, and visualized by the user.

While the example wearable computing device 502 is shown to have a touchscreen display, it should be understood that the wearable computing device 502 may not have any type of display unit, or may have any variety of audio and/or visual feedback components, such as light-emitting diodes (LEDs) (of various colors), buzzers, speakers, or a display with limited functionality. The wearable computing device 502 may be configured to be attached to the user's body, or clothing, such as a wrist bracelet, watch, ring, electrode, finger-clip, toe-clip, chest-strap, ankle strap or a device placed in a pocket. Additionally, the wearable computing device 502 may alternatively be embedded in something in contact with the user such as clothing, a mat under the user, a blanket, a pillow or another accessory involved in the activity of engaging in sleep.

The communication between wearable computing device 502 and external device 504 may be facilitated by one or more networks 506. In some implementations, one or more networks 506 include one or more of an ad hoc network, a peer to peer communication link, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or any other type of network. The communication between the wearable computing device 502 and external device 504 may also be performed through a direct wired connection. This direct-wired connection may be associated with any suitable or desirable communication protocol and/ or physical connector, such as Universal Serial Bus (USB), Micro-USB, WiFi, Bluetooth, FireWire, PCIe, or the like.

A variety of computing devices may be in communication with the wearable computing device 502, to facilitate sleep quality assessment. As depicted in FIG. 5, an example external computing device 504 is a smart phone with a display 508. An external computing device 504 may be any computing device capable of assessing values for one or more sleep quality metrics and/or a unified sleep score, such as, but not limited to, a smart phone, personal digital assistant (PDA), a mobile phone, a tablet, a personal computer, a laptop computer, a smart television, and/or a video game console. This example external computing device 504 illustrates that in some embodiments, through this networked relationship shown in FIG. 5, an external computing device 504 may be implemented to determine one or more sleep quality metrics, and/or a unified sleep score. For example, a user wears a wearable computing device 502 equipped as a bracelet with one or more physiological sensors but without a display. In this example, over the course of the night, as the user sleeps, the wearable computing device 502 records the user's heart beat, movement, body temperature and blood oxygen level as well as room temperature and ambient light levels, and periodically transmits this information to the external computing device 504. Alternatively, the wearable computing device 502 may store and transmit the collected physiological and/or environmental data and transmit this data to the external computing device 504 in response to a trigger, such as detection of the user being awake after a period of being asleep. In some implementations, the user must be awake for a threshold period of time to set this trigger (e.g., awake for at least 10 minutes), and/or awake for a threshold period of time after a threshold period of sleep has been experienced (e.g., awake for at least 5 minutes after having at least 6 hours of sleep). In some implementations, a trigger for determining one or more values of sleep quality metrics and/or a unified sleep score, is detection of a command performed at the external computing device 504, such as manual or automatic execution of an instruction to synchronize collected physiological and/or environmental data and determine the unified sleep score.

The example external computing device 504 illustrates that in some implementations, the external computing device 504 may present the values of one or more sleep quality metrics and/or a unified sleep score. This presentation may be made to the user (e.g., wearer) of the wearable computing device 502, or may, for example, be made to a sleep therapy provider for the user, such as a doctor or caregiver. In some implementations, the external computing device 504 determines one or more values for one or more sleep quality metrics and/or a unified sleep score and sends this information back to the wearable computing device 502 via the one or more networks 506, for presentation of such determined value or values to the user (e.g., wearer) of the wearable computing device. Additional information regarding presentation of a unified sleep score and/or values of one or more sleep quality metrics are discussed below, with respect to FIGS. 7A and 7B.

Figure 6:
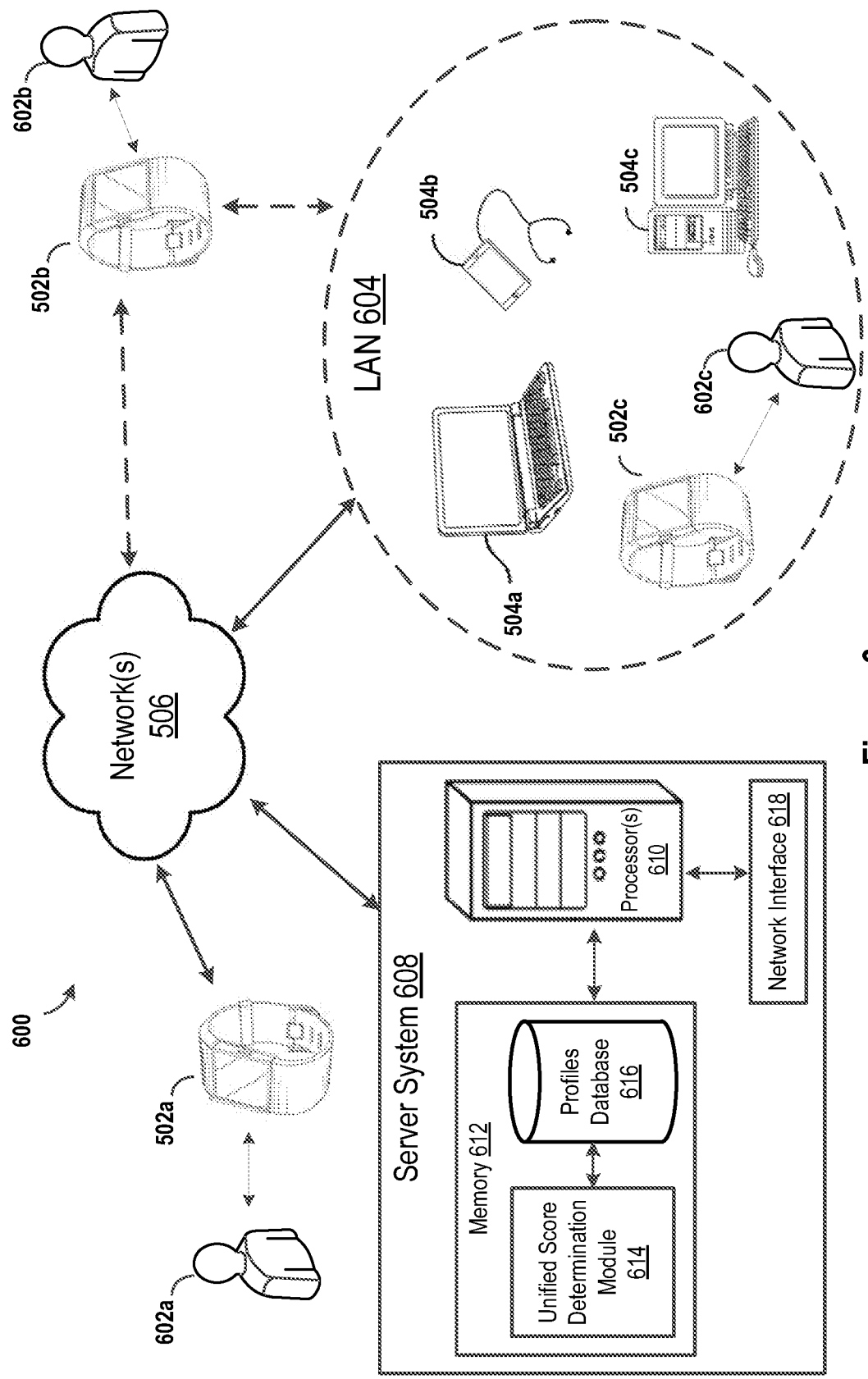
FIG. 6 illustrates a system of client devices and a server system for performing sleep quality assessment in accordance with one or more embodiments.

FIG. 6 illustrates a system 600 of client devices and a server system 608 for performing sleep quality assessment in accordance with one or more embodiments. In certain implementations, a sleep quality assessment system or platform, is implemented across a plurality of electronic devices. The wearable computing devices 502a, 502b and 502c may have characteristics similar to those described above with respect to wearable computing device 502 in FIG. 5, where each wearable computing device is coupled to a respective user 602a, 602b and 602c. The one or more networks 506 may have characteristics similar to those described above with respect to one or more networks 506 in FIG. 5. The example external computing devices 504a (e.g., a laptop computer), 504b (e.g., a smart phone), 504c (e.g., a personal computer) may have characteristics similar to those described above with respect to external computing device 504 in FIG. 5.

In some implementations, of a sleep quality assessment system 600, one or more wearable computing devices such as wearable computing device 502a are directly connected to one or more networks 506, connecting server system 608, and optionally connecting one or more external computing devices such as external computing devices 504a, 504b, and/or 504c. In some implementations, one or more external computing devices 504a, 504b and/or 504c are interconnected in a local area network (LAN) 604 (or another type of communication interconnection), which is connected to the one or more networks 506. The example LAN 604 may interconnect one or more external computing devices such as devices 504a, 504b, or 504c, as well as one or more wearable computing devices such as 502c. In some implementations, one or more wearable computing devices such as wearable computing device 502b are connected to one or more networks 506, indirectly, through LAN 604 to one or more external computing devices 504, which is/are connected to the one or more networks 506. In some implementations, one or more wearable computing devices such as wearable computing device 502b are connected to one or more networks 506 directly, and indirectly through LAN 604, as described above. For example, wearable computing device 502b is connected to smart phone 504b through a Bluetooth connection, smart phone 504b is connected to server system 608 through network 506, and wearable computing device 502b is also connected to server system 608 through network 506.

Sleep Quality Assessment Server

A sleep quality assessment system 600 may implement a server system 608 to collect detected physiological and/or environmental sensor readings from one or more wearable computing devices such as devices 502a, 502b and 502c as shown. In some implementations, server system 608 may also collect values of sleep quality assessment metrics and/or a unified sleep score from one or more wearable computing devices such as devices 502a, 502b and 502c and/or from one or more external computing devices such as devices 504a, 504b and 504c as shown. For example, wearable computing device 502a is not associated with an external computing device, therefore it transmits collected physiological data while user 602a sleeps to server system 608, which analyzes the received data to determine values of one or more sleep quality metrics and a unified sleep score, to transmit back to wearable computing device 502a. In another example, wearable computing device 502b transmits collected physiological data while user 602b sleeps (or has finished sleeping) to both server system 608 and external computing device 504a. In this example, external computing device 504a determines values for one or more sleep quality metrics and a unified sleep score, while server system 608 uses the received physiological data to update a user profile for user 602b, stored in profiles database 614.

In some implementations, server system 608 is implemented on one or more standalone data processing apparatuses or a distributed network of computers. In some embodiments, server system 108 also employs various virtual devices and/or services of third party service providers (e.g., third-party cloud service providers) to provide the underlying computing resources and/or infrastructure resources of server system 108. In some embodiments, server system 108 includes, but is not limited to, a handheld computer, a tablet computer, a laptop computer, a desktop computer, or a combination of any two or more of these data processing devices or other data processing devices.

Server system 608 may include one or more processors or processing units 610 (e.g., CPUs) and one or more network interfaces 618 including an I/O interface to external computing devices and wearable computing devices. In some implementations, server system 608 includes memory 612, and one or more communication buses for interconnecting these components. Memory 612 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. Memory 612, optionally, includes one or more storage devices remotely located from one or more processing units 610. Memory 612, or alternatively the non-volatile memory within memory 612, includes a non-transitory computer readable storage medium. In some implementations, memory 612, or the non-transitory computer readable storage medium of memory 612, stores one or more programs, modules, and data structures. These programs, modules and data structures may include, but not be limited to one or more of an operating system including procedures for handling various basic system services and for performing hardware dependent tasks, a network communication module for connecting server system 608 to other computing devices (e.g., wearable computing devices 502*a*, 502*b* and 502*c* and/or external computing devices 504*a*, 504*b* and 504*c*) connected to one or more networks 506 via one or more network interfaces 618 (wired or wireless).

Memory 612 may also include a unified score determination module 614 for using collected physiological and/or environmental data of one or more users (e.g., received from one or more wearable computing devices or external computing devices), to determine values of one or more sleep quality metrics and/or a unified sleep score, as described earlier in the present disclosure, with respect to FIGS. 3, 4A and 4B. Memory 612 may also include a profiles database 616 storing user profiles for users of the sleep quality assessment system 600, where a respective user profile for a user may include a user identifier (e.g., an account name or handle), login credentials to the sleep quality assessment system, email address or preferred contact information, wearable computing device information (e.g., model number), demographic parameters for the user (e.g., age, gender, occupation, etc.), historical sleep quality information and identified sleep quality trends of the user (e.g., particularly restless sleeper). In some implementations, collected physiological information of a plurality of users (such as users 602*a*, 602*b* and 602*c*) of the sleep quality assessment system 600 provides for more robust population-normalized sleep metrics, as described above with respect to FIGS. 3, 4A and 4B. For example, user 602*a* is a 35 year old female veterinarian and user 602*b* is a 34 year old female veterinarian, and each of their respective historical sleep quality physiological data and/or metrics are used in the determination of one or more population-normalized sleep quality metrics for each other, due to their closely aligned demographic characteristics. In some implementations, a user may opt in or opt out of providing sleep quality assessment information to a population-normalization determination for other users. In some implementations, a user's sleep quality information may be incorporated into population-normalized sleep quality metric information used to determine that user's own values for one or more sleep quality metrics.

Presentation of Unified Sleep Quality Score

FIG. 7A illustrates embodiments of wearable computing devices 700*a* and 700*b*, each having displays for presenting a representation of a unified sleep score in accordance with one or more embodiments. The computing devices 700*a* and 700*b* of FIG. 7A each illustrate a generally rectangular display. Computing device 700*a* illustrates that some wearable computing devices may have a set of light-emitting diodes (LEDs), to indicate a status, or in this context, a representation of a unified sleep quality score. For example, 3 out of 4 illuminated LEDs, as shown in display 702*a*, may indicate a moderately good unified sleep quality score.

In certain embodiments, computing device 700*b* may be configured to display text and/or other visual elements on the display 702*b*. The display 702*b* of the computing device 700*b* may represent a relatively small display, wherein portrayal of extensive information may be undesirable and/or impractical. As a result, display 702*b* of a wearable computing device 700*b* with limited display capability, may simply portray a numerical (e.g., 45, or 8/10) and/or subjective representation (e.g., good, bad, neutral) of the unified sleep quality score.

FIG. 7B illustrates embodiments of wearable computing devices having touchscreen displays for presenting a representation of a unified sleep score in accordance with one or more embodiments. FIG. 7B illustrates wearable computing devices 704*a* and 704*b* having a generally rectangular, horizontally-arranged, display 706*a* and 706*b*, respectively. Display 706*a* illustrates that in some implementations, a unified sleep quality score may be portrayed along with more detailed information about the sleep quality metrics contributing to the unified sleep quality score. In some implementations, a user may be able to scroll through this detailed information on display 706*a*. Display 706*b* illustrates that a representation of a unified sleep quality score may be in the form of a graphic, emoji, background color or another audio-visual representation other than numbers or text.

Methods for Assessing Sleep Quality

Figure 8:
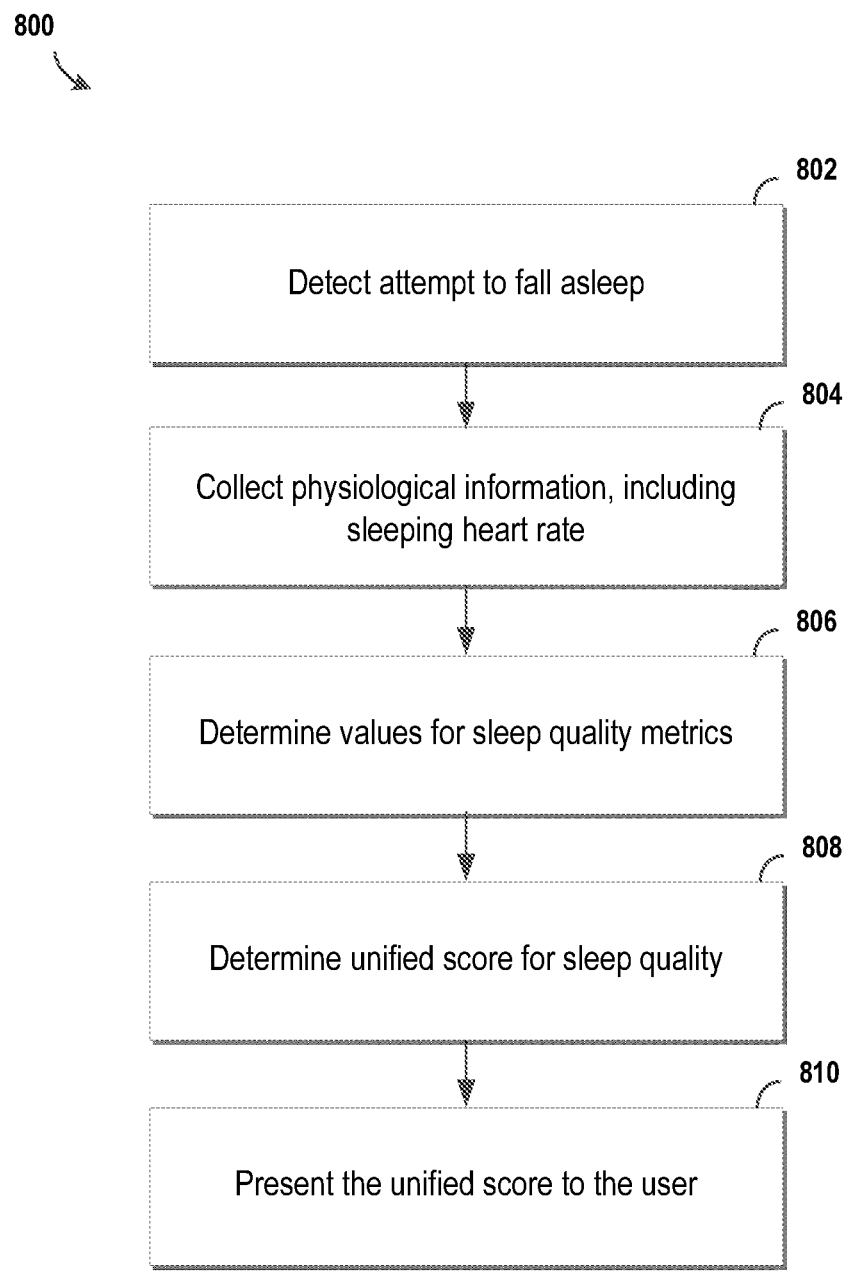
FIG. 8 illustrates a flow diagram for a process of determining a sleep quality assessment in accordance with one or more embodiments.

FIG. 8 illustrates a flow diagram for a process 800 for determining a sleep quality assessment in accordance with the present disclosure. In certain embodiments, the process 800 may be performed at least in part by a computing device having one or more physiological and/or environmental sensors and/or control circuitry of the computing device. For example, a user may be wearing a computing device on a wrist or other body part, or otherwise have the computing device attached to him or her, when at least part of the process 800 is performed. The process 800 may be performed in order to assess the quality of sleep experienced by a user, using one or more sleep quality metrics based off of detected physiological and/or environmental information. In some implementations, process 800 is performed at least in part by a plurality of electronic devices (e.g., a wearable computing device and an external computing device), and in some implementations, process 800 is performed at least in part by a sleep quality assessment server (e.g., server system 608 as described with respect to FIG. 6 and a wearable computing device).

In certain embodiments, prior to execution of the first step 802 of the process 800, a user may have been detected to be in a wakeful state. For example, the user is detected to be awake and not attempting to sleep from 7:01 AM until 10:59 PM. When the user attempts to fall asleep, one or more measurable physiological parameters relating to sleep quality metrics may be triggered to be detected. In certain embodiments, the process 800 may be implemented in connection with a wearable computing device that may be worn, for example, about a wrist or other member of the user. In certain embodiments, the sleep quality assessment process 800 may be initiated when the user puts on the device and/or contacts a device with the user's skin and/or lays down in a reclined position. Alternatively, sleep quality assessment processes in accordance with the present disclosure may be initiated after a predetermined period of time in an idle state, or in connection with a request to initiate a sleep assessment program.

At block 802, the process 800 involves detecting an attempt by a user to fall asleep, or receiving one or more signals indicating an attempt by the user to fall asleep. For example, a user is wearing a computing device that detects that the user has entered a reclined position, that the ambient light is low and/or that the device is in contact with the user but is relatively motionless. In some implementations, process 800 includes detecting an onset of sleep by the user, or receiving one or more signals indicating an onset of sleep by the user and determining a duration of time from the attempt to fall asleep to the onset of sleep. In some implementations, sleep attempt detection is based automatically off of one or more physiological and/or environmental sensor readings, while in some implementations it is based off of manual input from the user (e.g., pressing a button on a wearable computing device or indicating attempt to sleep in an application on a wearable or external computing device).

At block 804, the process 800 involves collecting (or receiving) physiological information associated with the user, including at least one sleeping heart rate. For example, the sleeping heart rate may be an average of periodically measured heart rate values of a user during a total duration of sleep (e.g., during a night of sleep). In some implementations, the physiological information is collected periodically and/or upon detection of a change in some condition (e.g., movement). In some implementations, physiological information is still collected while the user is awake, such as in a period of time between an attempt to fall sleep and the onset of sleep, or during a period of wakefulness before the user awakens for a long period of time (e.g., waking up in the morning). In some implementations, collecting physiological information about the user includes collecting one or more sets of values associated with: movement of the user, total sleep duration, total deep sleep duration, duration of wake time after sleep onset (WASO), total rapid-eye-movement (REM) sleep duration, total light sleep duration, breathing patterns of the user, breathing disturbances of the user and temperature of the user.

At block 806, the process 800 involves determining respective values for one or more sleep quality metrics, based at least in part on the collected physiological information. In some implementations, determining respective values for one or more sleep quality metrics includes using at least one wakeful resting heart rate of the user. For example, determining a value for a heart rate metric includes comparing an average sleeping heart rate of the collected physiological information, and an average wakeful resting heart rate detected and calculated before the user attempts to fall asleep. In some implementations, the wakeful resting heart rate is determined periodically during a period of extended wakefulness before the user enters a state of sleep. In some implementations, the wakeful resting heart rate is the lowest resting heart rate value detected while the user is awake. In some implementations, determining respective values for the one or more sleep quality metrics includes comparing the at least one sleeping heart rate of the user and the at least one wakeful resting heart rate of the user. In some implementations, determining respective values for the one or more sleep quality metrics includes comparing the at least one sleeping heart rate of the user to a threshold value.

In certain embodiments, the one or more sleep quality metrics includes a first set of sleep quality metrics associated with sleep quality of a plurality of users, and a second set of sleep quality metrics associated with historical sleep quality of the user. In certain embodiments, process 800 further includes detecting that the user is awake after the detected onset of sleep, and determining the respective values for one or more sleep quality metrics, in response to detecting that the user is awake.

At block 808, the process 800 includes determining a unified score for sleep quality of the user, based at least in part on the respective values of the one or more sleep quality metrics. In certain embodiments, determining the unified score for sleep quality includes determining a respective metric-score for each of the one or more sleep quality metrics and applying a respective weighting for each of the one or more sleep quality metrics. In some embodiments, process 800 includes collecting sleep quality feedback information from the user and determining the unified score for sleep quality of the user based at least in part on the collected sleep quality feedback information.

At block 810, the process 800 involves presenting a representation of the unified score to the user, or generating instructions to provide a representation of the unified score to the user. For example, as shown in FIGS. 7A and 7B, a representation of the unified score may vary depending on the audio, visual feedback capability of a wearable and/or biometric monitoring device. A representation of the unified score may include any of alphanumeric characters, graphics, sounds, lights, patterns and animations. In another example, server system 608 of FIG. 6 sends instructions to a wearable computing device to present a unified sleep quality assessment score of 85, on a display of the wearable computing device.

Figure 9:
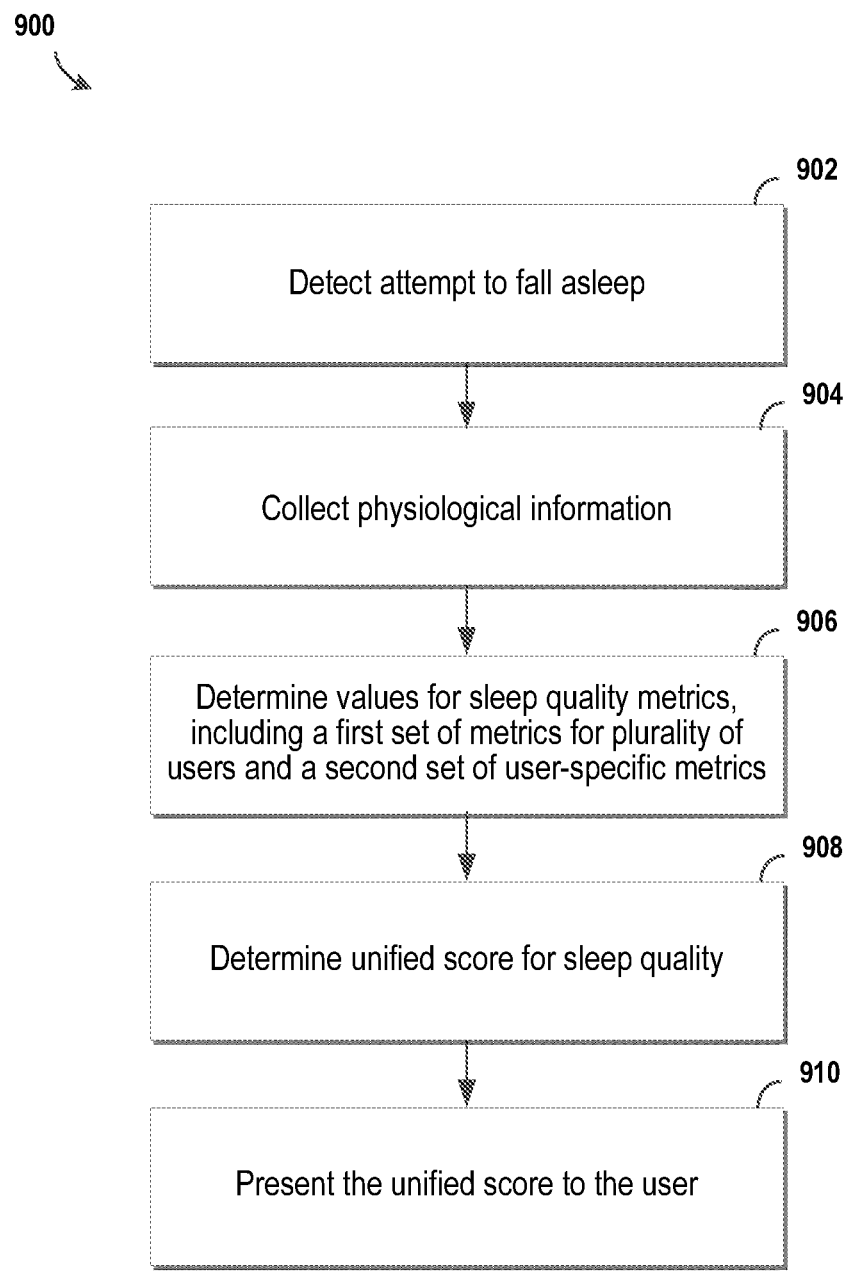
FIG. 9 illustrates a flow diagram for a process of determining a sleep quality assessment in accordance with one or more embodiments.

FIG. 9 illustrates a process 900 for determining a sleep quality assessment in accordance with one or more embodiments disclosed herein. The process 900 may be performed at least in part by a computing device having one or more physiological and/or environmental sensors and/or control circuitry of the computing device. For example, the user may be wearing a computing device on a wrist or other body part, or otherwise have the computing device attached to him or her, when performing at least part of the process 900. The process 900 may be performed in order to assess the quality of sleep experienced by a user, using one or more sleep quality metrics based off of detected physiological and/or environmental information. In some implementations, process 900 is performed at least in part by a plurality of electronic devices (e.g., a wearable computing device and an external computing device), and in some implementations, process 900 is performed at least in part by a sleep quality assessment server (e.g., server system 608 as described with respect to FIG. 6 and a wearable computing device).

At block 902, the process 900 involves detecting an attempt by a user to fall asleep or receiving one or more signals indicating an attempt by the user to fall asleep. For example, a user is wearing a computing device that detects that the user has entered a reclined position, that the ambient light is low and/or that the device is in contact with the user but is relatively motionless. In some implementations, process 900 includes detecting an onset of sleep by the user, or receiving one or more signals indicating an onset of sleep by the user and determining a duration of time from the attempt to fall asleep to the onset of sleep.

At block 904, the process 900 involves collecting physiological information associated with the user. In some implementations, collecting physiological information associated with the user includes collecting one or more sets of values associated with: movement of the user, total sleep duration, total deep sleep duration, duration of wake time after sleep onset (WASO), total rapid-eye-movement (REM) sleep duration, total light sleep duration, breathing patterns of the user, breathing disturbances of the user and temperature of the user.

At block 906, the process 900 involves determining respective values for one or more sleep quality metrics, based at least in part on the collected physiological information, wherein the one or more sleep quality metrics includes a first set of sleep quality metrics associated with sleep quality of a plurality of users, and a second set of sleep quality metrics associated with historical sleep quality of the user. In some implementations, determining respective values for one or more sleep quality metrics includes using at least one wakeful resting heart rate of the user. For example, determining a value for a heart rate metric includes using an average sleeping heart rate of the collected physiological information, and an average wakeful resting heart rate detected and calculated before the user attempts to fall asleep. In some implementations, determining respective values for the one or more sleep quality metrics includes comparing the at least one sleeping heart rate of the user and the at least one wakeful resting heart rate of the user. In certain embodiments, process 900 further includes detecting that the user is awake after the detected onset of sleep, or receiving one or more signals indicating that the user is awake, and determining the respective values for one or more sleep quality metrics, in response to detecting that the user is awake.

At block 908, the process 900 includes determining a unified score for sleep quality of the user, based at least in part on the respective values of the one or more sleep quality metrics. In certain embodiments, determining the unified score for sleep quality includes determining a respective metric-score for each of the one or more sleep quality metrics and based at least in part on a respective weighting for each of the one or more sleep quality metrics. In some embodiments, process 900 includes collecting sleep quality feedback information from the user or receiving collected sleep quality information and determining the unified score for sleep quality of the user based at least in part on the collected sleep quality feedback information At block 910, the process 900 involves presenting a representation of the unified score to the user or generating a representation of the unified score to present to the user. For example, as shown in FIGS. 7A and 7B, a representation of the unified score may vary depending on the audio. visual feedback capability of a wearable and/or biometric monitoring device. A representation of the unified score may include any of alphanumeric characters, graphics, sounds, lights, patterns and animations. In another example, server system 608 of FIG. 6 sends instructions to a wearable computing device to present a unified sleep quality assessment score of 85, on a display of the wearable computing device.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Certain methods and/or processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A wearable device, comprising:
   a housing;
   one or more physiological sensors disposed in the housing, the one or more sensors operable to capture one or more signals, the one or more signals including signals representative of movement;
   one or more processors disposed in the housing;
   a display; and
   control circuitry configured to:
      detect a lack of movement for a threshold period of time;
      collect physiological data, including at least one sleeping heart rate;
      determine respective values for one or more sleep quality metrics, based at least in part on the collected physiological data and at least one wakeful resting heart rate; and
      present, on the display, a representation of a score for sleep quality, the score for sleep quality based at least in part on the respective values of the one or more sleep quality metrics.

2. The wearable device of claim 1, wherein the one or more sleep quality metrics includes a first set of sleep quality metrics associated with sleep quality of a plurality of users, and a second set of sleep quality metrics associated with historical sleep quality of one user.

3. The wearable device of claim 1, wherein the control circuitry and the one or more processors being configured to determine the score for sleep quality includes being configured to:
   determine a respective metric-score for each of the one or more sleep quality metrics; and
   apply a respective weighting for each of the one or more sleep quality metrics.

4. The wearable device of claim 1, wherein the control circuitry and the one or more processors are further configured to determine the at least one wakeful resting heart rate before detecting the lack of movement.

5. The wearable device of claim 1, wherein the physiological data includes one or more sets of values associated with at least one of: movement, total sleep duration, total deep sleep duration, duration of wake time after sleep onset, total rapid-eye-movement sleep duration, total light sleep duration, breathing patterns, breathing disturbances, and temperature.

6. The wearable device of claim 1, wherein the control circuitry and the one or more processors are further configured to:
   collect sleep quality feedback; and
   determine the score for sleep quality based at least in part on the collected sleep quality feedback.

7. The wearable device of claim 1, wherein the control circuit and the one or more processors being configured to determine respective values for the one or more sleep quality metrics includes being configured to compare the at least one sleeping heart rate and the at least one wakeful resting heart rate.

8. The wearable device of claim 1, wherein the control circuitry and the one or more processors are further configured to:
   detect an onset of sleep; and
   determine a duration of time from the lack of movement to the onset of sleep.

9. The wearable device of claim 8, wherein the control circuitry and the one or more processors are further configured to:
   detect an awake status after the onset of sleep; and
   determine the respective values for one or more sleep quality metrics, in response to detecting the awake status.

10. A computer-implemented method, comprising:
    receiving one or more signals indicating a lack of movement for a threshold period of time;
    receiving physiological data including at least one sleeping heart rate, the physiological data generated by one or more physiological sensors;
    determining respective values for one or more sleep quality metrics based at least in part on the physiological data and at least one wakeful resting heart rate; and
    determining a score for sleep quality, based at least in part on the respective values of the one or more sleep quality metrics;
    presenting, on the display, a representation of a score for sleep quality, the score for sleep quality based at least in part on the respective values of the one or more sleep quality metrics.

11. The computer-implemented method of claim 10, wherein the at least one wakeful resting heart rate includes a representative value of one or more of heart rate values during a period of relative inactivity.

12. The computer-implemented method of claim 10, wherein the one or more sleep quality metrics includes a first set of sleep quality metrics associated with sleep quality of a plurality of users, and a second set of sleep quality metrics associated with historical sleep quality of one user.

13. The computer-implemented method of claim 10, wherein determining the score for sleep quality includes:
    determining a respective metric-score for each of the one or more sleep quality metrics; and
    applying a respective weighting for each of the one or more sleep quality metrics.

14. The computer-implemented method of claim 10, wherein the at least one wakeful resting heart rate is determined before receiving one or more signals indicating the lack of movement.

15. The computer-implemented method of claim 10, wherein the physiological data includes one or more sets of values associated with at least one of: movement, total sleep duration, total deep sleep duration, duration of wake time after sleep onset, total rapid-eye-movement sleep duration, total light sleep duration, breathing patterns, breathing disturbances, and temperature.

16. The computer-implemented method of claim 10, further comprising:
    receiving sleep quality feedback; and
    determining the score for sleep quality based at least in part on the sleep quality feedback.

17. The computer-implemented method of claim 10, wherein determining the respective values for the one or more sleep quality metrics includes comparing the at least one sleeping heart rate and the at least one wakeful resting heart rate.

18. The computer-implemented method of claim 10, further comprising:
   receiving one or more signals indicating an onset of sleep; and
   determining a duration of time from the lack of movement to the onset of sleep.

19. The computer-implemented method of claim 18, further comprising:
   receiving one or more signals indicating an awake status after the onset of sleep; and
   determining the respective values for one or more sleep quality metrics, in response to receiving one or more signals indicating the awake status.

20. A computing system, comprising:
   one or more processors; and
   memory including instructions that, when executed by the at least one processor, cause the computing system to:
   receive movement data from a wearable device, the movement data including a lack of movement for a threshold period of time;
   collect, from the wearable device, physiological data including at least one sleeping heart rate;
   determine respective values for one or more sleep quality metrics, based at least in part on the collected physiological data and at least one wakeful resting heart rate; and
   determine a score for sleep quality, based at least in part on the respective values of the one or more sleep quality metrics;
   present, on the display, a representation of a score for sleep quality, the score for sleep quality based at least in part on the respective values of the one or more sleep quality metrics.

* * * * *